United States Patent
Chaffey et al.

(10) Patent No.: US 9,140,487 B2
(45) Date of Patent: Sep. 22, 2015

(54) BIOLOGICAL SAMPLE STORAGE AND MONITORING SYSTEM

(75) Inventors: Jason Philip Chaffey, Blackburn South (AU); Miroslav Miljanic, Dandenong North (AU)

(73) Assignee: BLUECHIP LIMITED, Scoresby (AU)

( * ) Notice: Subject to any disclaimer, the term of this patent is extended or adjusted under 35 U.S.C. 154(b) by 410 days.

(21) Appl. No.: 13/490,090

(22) Filed: Jun. 6, 2012

(65) Prior Publication Data

US 2012/0293338 A1  Nov. 22, 2012

Related U.S. Application Data

(63) Continuation-in-part of application No. PCT/AU2010/001645, filed on Dec. 7, 2010.

(51) Int. Cl.
*G08B 23/00* (2006.01)
*F25D 29/00* (2006.01)
*A01N 1/02* (2006.01)
(Continued)

(52) U.S. Cl.
CPC .............. *F25D 29/00* (2013.01); *A01N 1/0252* (2013.01); *A01N 1/0257* (2013.01); *B01L 3/545* (2013.01); *B01L 7/50* (2013.01); *G01K 1/022* (2013.01); *G01K 1/024* (2013.01); *G01K 7/32* (2013.01);
(Continued)

(58) Field of Classification Search
CPC .......... C12N 5/11; C12N 15/85; C12N 15/52; C12N 15/87; C12N 9/1051; C12N 9/16; C12N 9/2402; C12N 9/2445; C12N 9/6451; C12N 9/88; C12N 9/93; C12N 5/0605; C12N 7/00

USPC .......... 340/870.02, 572.1, 10.1, 505, 870.01; 62/63, 80.127; 73/863.11; 435/1.1; 700/125; 374/13.001, 13.004
See application file for complete search history.

(56) References Cited

U.S. PATENT DOCUMENTS 5,565,858 A * 10/1996 Guthrie ....................... 340/10.33
6,677,857 B2 * 1/2004 Bara et al. .................. 340/572.1
(Continued)

FOREIGN PATENT DOCUMENTS

WO    2004084131 A1    9/2004

OTHER PUBLICATIONS

Lin, J. et al., "Wireless Temperature Sensing using a Passive RFID Tag with Film Bulk Acoustic Resonator", Ultrasonics Symposium, 2008, IUS 2008. IEEE, pp. 2209-2212, Nov. 2-5, 2008, DOI: 10.1109/ULTSYM.2008.0547.

(Continued)

*Primary Examiner* — Eric M Blount
(74) *Attorney, Agent, or Firm* — Maschoff Brennan

(57) ABSTRACT

A method of maintaining a thermal history (369; 699) of samples stored in a temperature-controlled sample storage system is provided. The system can include: one or more containers (218, 220; 522) each storing one of the samples; one or more storage objects (210-216, 208; 510, 516-518, 520; 654-660, 662) each housing one or more containers or other storage objects; one or more structures (200-206; 512; 650) defining a temperature-controlled storage environment and housing the one or more storage objects; machine readable tags (14) each of which is associated with a separate container and storage object, each tag encoding an identification code and having a temperature-dependant characteristic; and an interrogator (12) for reading the identification code and the temperature-dependant characteristic.

17 Claims, 20 Drawing Sheets

(51) Int. Cl.
  *B01L 3/00* (2006.01)
  *B01L 7/00* (2006.01)
  *G01K 1/02* (2006.01)
  *G01K 7/32* (2006.01)

(52) U.S. Cl.
  CPC ....... *B01L 2300/022* (2013.01); *F25D 2500/06* (2013.01)

(56) References Cited

U.S. PATENT DOCUMENTS 7,102,519 B2     9/2006   Lyon et al.
7,958,791 B2 *   6/2011   Zimmermann et al. ... 73/863.11
8,346,382 B2 *   1/2013   Davidowitz et al. .......... 700/125
8,451,138 B2 *   5/2013   Zimmermann et al. . 340/870.31
2005/0069861 A1  3/2005   Zimmermann et al.

OTHER PUBLICATIONS

Startup bluechiip introduces robust mechanical alternative to RFID chips, based on MEMS resonators, MEMSentry Article, Sep. 2009, pp. 12-14, Issue No. 44, Yole Development SA, Lyon-France.

International Search Report dated Jan. 18, 2011 as received in related application No. PCT/AU2010/001645.

* cited by examiner

BIOLOGICAL SAMPLE STORAGE AND MONITORING SYSTEM

FIELD OF THE INVENTION

This invention relates to the storage and monitoring of samples in a temperature-controlled storage environment, such as the cold storage of biological samples in cryogenic tanks.

BACKGROUND OF THE INVENTION

Biological samples are collected and stored in many different types of facilities, for a great variety of applications. Such applications include the storage of samples collected during clinical trials in pharmaceutical companies, research samples used in university laboratories, samples archived in hospitals, samples used in the discovery of biological markers for diagnostic testing, forensic samples from crime or disaster scenes and so on. Cord blood and stem cell samples are one example of a biological sample required to be stored in the very low temperatures provided by liquid nitrogen. In order to ensure sample integrity, both samples are required to be typically maintained at temperatures of less than minus 150° C.

Typically, in each of the systems for storing biological samples, each of a large number of samples is stored in its own small plastic bag, tube or other container. Tracking of the samples is done by reading hand written labels or barcodes on the containers. A number of difficulties arise with this approach, including poor writing surfaces, little room for extensive information, ice impaired reading by humans or optical scanners, difficulty in locating a particular sample amongst the many thousands of samples maintained in a cryogenic tank to name but a few.

An inherent operating condition within a cryogenic tank is the thick fog created by the liquid nitrogen. This fog makes it difficult to identify racks that stand in the tank when attempting to identify a desired biological sample. It is current practice at cryopreservation facilities to remove racks containing biological samples from a cryogenic tank in order to visually identify a desired biological sample. In this case, not only is the sample which is desired to be identified exposed to the ambient environment, but so are other biological samples contained in that same rack.

It would be desirable to provide a system for storing and monitoring samples which enables improved operating practices to be followed from those described above. It would also be desirable to provide a system for storing and monitoring samples which ameliorates and/or overcomes one or more problems or inconveniences of the prior art.

The above discussion of background art is included to explain the context of the present invention. It is not to be taken as an admission that any of the documents or other material referred to was published, known or part of the common general knowledge at the priority date of any one of the claims of this specification.

SUMMARY OF THE INVENTION

One aspect of the invention provides a method of maintaining a thermal history of samples stored in a temperature-controlled sample storage system, the system including one or more containers each storing one of the samples; one or more storage objects each housing one or more containers or other storage objects; one or more structures defining a temperature-controlled storage environment and housing the one or more storage objects; machine readable tags each of which is associated with a separate container and storage object, each tag encoding an identification code and having a temperature-dependant characteristic; and an interrogator for reading the identification code and the temperature-dependant characteristic, the method including the steps of:

a) monitoring the temperature in each temperature-controlled storage environment;

b) interrogating a database to determine one or more specific storage objects housing a particular container within a specific structure;

c) locating one of the specific storage objects housing the particular container by reading the identification code of the machine-readable tag associated with that specific storage object;

d) reading the value of the temperature dependant characteristic of the machine-readable tag associated with the specific storage object located in step c);

e) storing the read identification code and value of the temperature-dependant characteristic in the database;

f) removing the particular container, or another of the specific storage objects in which the particular container is stored, from the storage object located in step b);

g) repeat steps c) to f) until the particular container is removed; and h) returning the one or more specific storage objects to the specific structure.

In one or more embodiments, the method may further include the step of:

determining whether any of the values of the temperature dependant characteristic exceed a temperature limit.

In this case, the method may further include the step of:

triggering an alarm condition when the value exceeds the temperature limit.

In one or more embodiments, the method may further include the step of:

determining whether any of the values of the temperature dependant characteristic exceeds any of a plurality of temperature limits.

In this case, the method may further include the step of:

triggering an alarm condition when the value exceeds any one of the temperature limit.

Moreover, the method may further include the step of:

providing a different response depending upon which of the temperature limits are exceeded.

In one or more embodiments, the method may further include the step of:

prior to step c), locating the specific structure housing the particular container by reading the identification code of the machine-readable tag associated with that structure.

In one or more embodiments, the method may further include the step of retrievably housing each container in the structure by:

reading the identification code of the machine-readable tag associated with each container;

reading the identification code of the machine-readable tag associated with each storage object in which the container is housed;

storing the read identification codes in the database for subsequent interrogation.

In one or more embodiments, each machine readable tag may include a plurality of resonant members.

In this case, at least one of the resonant members may have the temperature-dependant characteristic.

In one or more embodiments, the resonant members may have different resonant frequencies from each other.

In one or more embodiments, the resonant members may be vibrated by a Lorentz-type force on application of an excitation signal to the tag.

In one or more embodiments, the temperature-dependant characteristic may be a shift in resonant frequency of the at least one resonant member as a function of temperature.

In one or more embodiments, a first coil antenna is coupled to the plurality of resonant members, wherein the interrogator includes signal processing circuitry and a reading head in communication with signal processing circuitry, and the reading head includes an interrogation coil, the method further including the steps of:

positioning the interrogation coil proximate the coil antenna; and generating an interrogation signal in the interrogation coil so as to induce an excitation signal in the coil antenna.

In this case, the step of positioning the interrogation coil proximate the coil antenna may include locating one of the interrogation coil and the antenna coil inside the other during tag reading.

Under such conditions, one or both of the interrogation coil and the antenna coil may have a helical form.

The step of positioning the interrogation coil proximate the coil antenna may include concentrically locating the interrogation coil and the antenna coil during tag reading.

Embodiments of the invention will now be described, by way of example only, with reference to the accompanying drawings. It is to be understood that the particularity of the drawings and embodiments does not supersede the generality of the preceding description of the invention.

DETAILED DESCRIPTION OF EMBODIMENTS OF THE INVENTION

Figure 1:
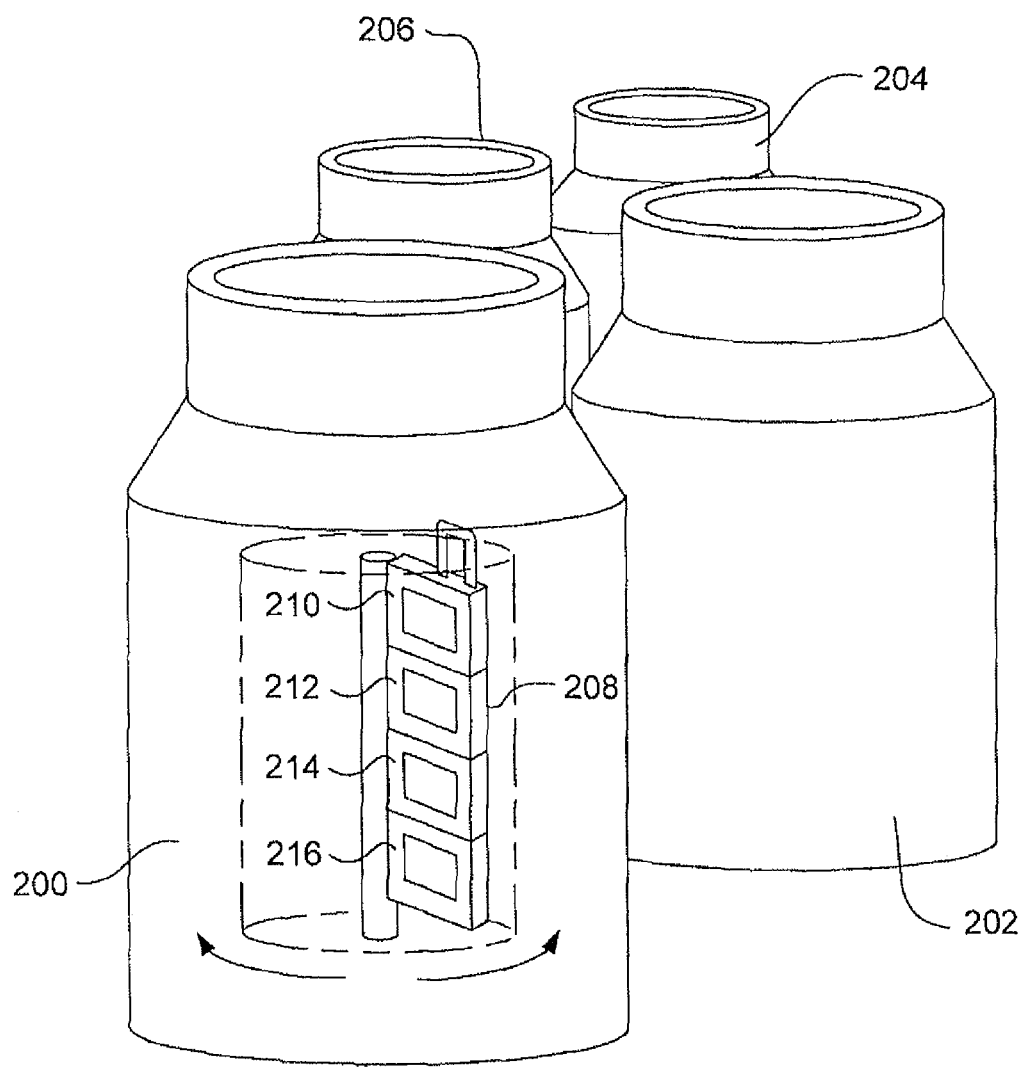
FIG. 1 is a schematic diagram depicting a bank of temperature controlled storage vessels, in this case cryogenic tanks, for housing biological samples.

FIG. 1 depicts a group of structures defining a temperature-controlled storage environment, in this case cryogenic tanks 200 to 206 which are used to store biological samples. Within each cryogenic tank is located a series of racks, an exemplary one of which is referenced 208. Each rack houses a series of cassettes 210 to 216. It will be appreciated that a cryogenic tank is merely one example of a structure defining a temperature-controlled storage environment suitable for use with the present invention, and that other suitable structures, could be envisaged.

Figure 2:
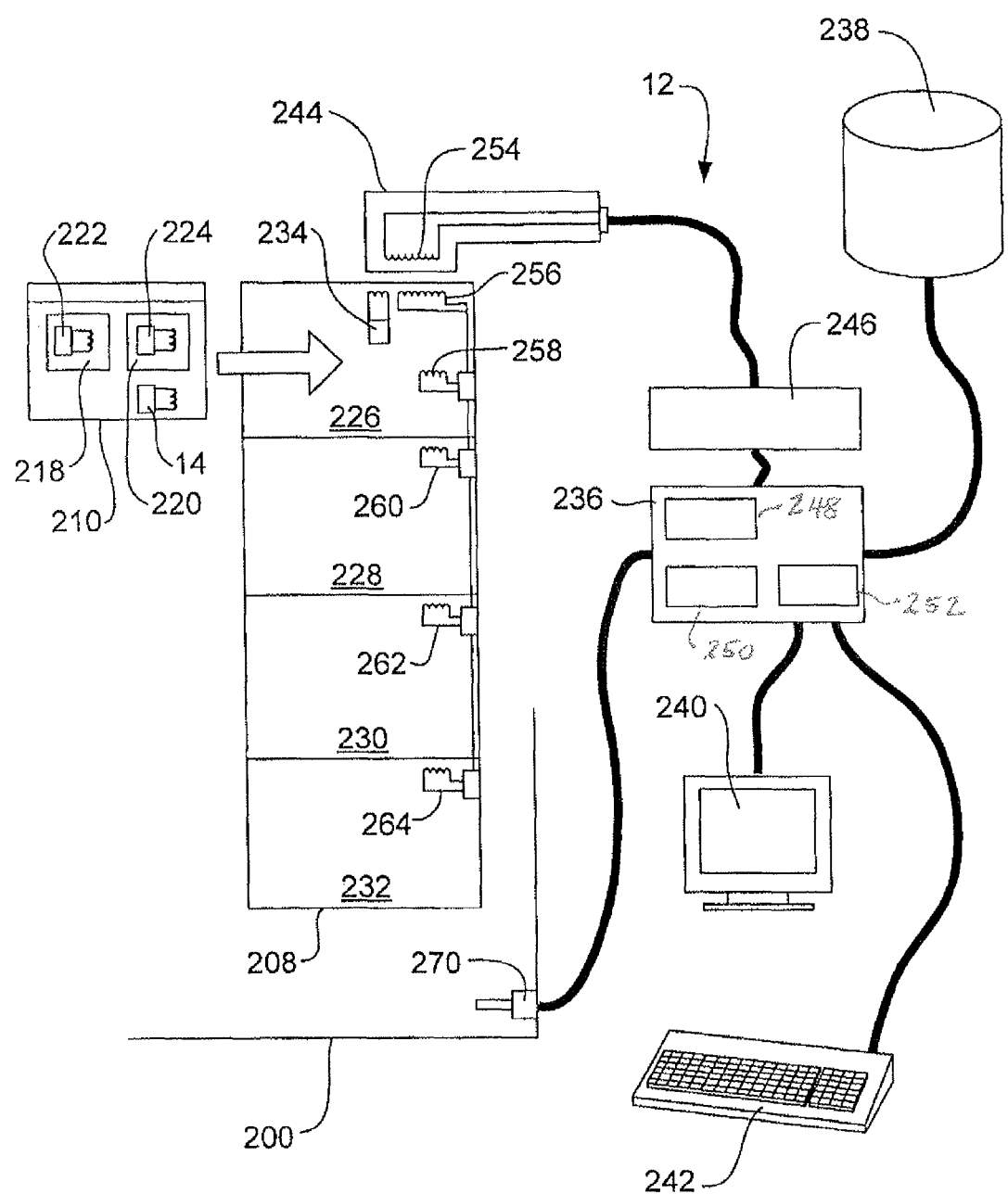
FIG. 2 is schematic diagram depicting one of the cryogenic tanks shown in FIG. 1, a rack and containers housed within that cryogenic tank, together with an interrogator, controller and database forming part of a system for storing and monitoring samples in accordance with one embodiment of the present invention.

As can be better appreciated from FIG. 2, each rack is adapted to house a series of containers in predefined rack positions or slots. In this example, the cassette 210 is adapted to house stem cell bags 218 and 220 each of which contains blood or another biological sample. In this case, the stem cell bags form containers of a hierarchical level and adapted to be housed in one or more other containers (in this case, cassettes) at a higher hierarchical level. In other embodiments of the invention, one or more containers of that first hierarchical level may be adapted to house one or more other containers (such as test tubes) at a lower hierarchical level.

A machine readable tag is associated with a group of one or more samples. In this case, the samples are stored within the stem cell bags 218 and 220, and the machine readable tag associated with those samples is the tag 14 affixed to or formed within the cassette 210. In other embodiments of the invention though, tags, such as those referenced 222 and 224 may be affixed to the stem cell bags directly so that there is a direct association with each of these tags and the lower most hierarchical level of containers within which the biological samples are stored.

The cassette 210 is shown in FIG. 2 as being insertable into rack position 226, however the cassette 210 is equally able to be inserted into the other depicted rack positions 228 to 232. In this example, a further tag 234 is affixed to the rack 208.

An interrogator for reading information from each of the various tags affixed to or located within the rack 234, a controller 236 and associated database 238 for recording and maintaining a record of the information captured by the interrogator, as well as a display 240 and data/command input device 242, such as a keyboard. The interrogator includes a manually operable reading head or "wand" 244 adapted to be moved by an operator to be physically proximate the rack 208. The interrogator 12 also includes a main body 246 housing signal processing circuitry in communication with the central controller 236. The central controller includes a processor 248, a first memory device 250 for maintaining a set of instructions, such as a computer programme, for causing operation of the central controller as well as a second memory device 252 for maintaining data generated during operation of the central controller.

The interrogator is adapted to generate an excitation signal in an interrogation coil 254 housed in the want 244. The excitation signal is transferred by induction to the corresponding coil 256 within the rack 208. A corresponding excitation signal is generated in each of rack excitation coils 258 to 272 in order to generate, again by induction, a corresponding excitation signal in antennas forming part of each of the tags located in a particular rack slot. Switching devices may be provided in order that the coils 258 to 264 are each independently activated.

Figure 3:
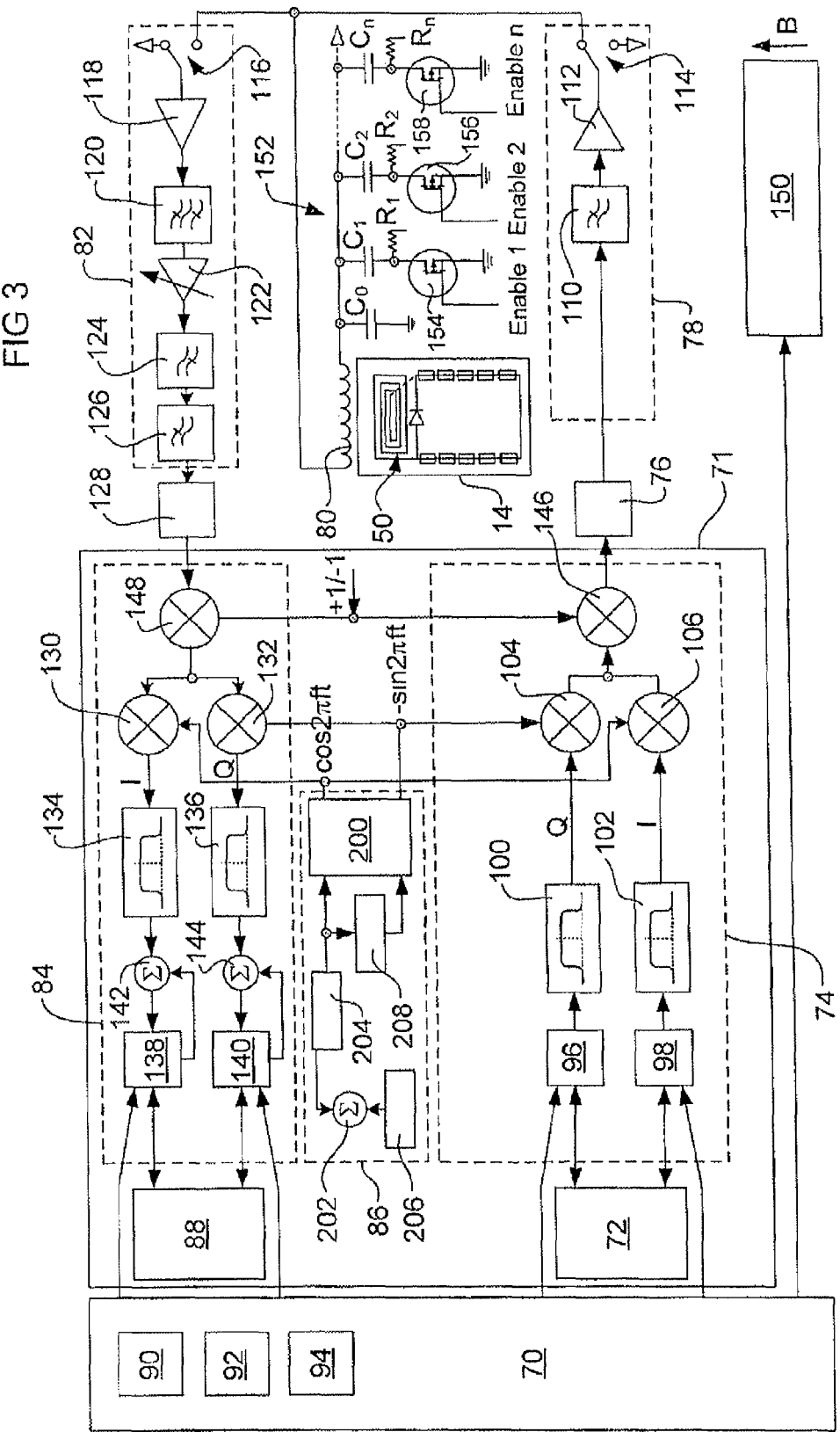
FIG. 3 is a detailed schematic diagram of the interrogator and an exemplary tag forming part of the system depicted in FIG. 2.
Figure 4:
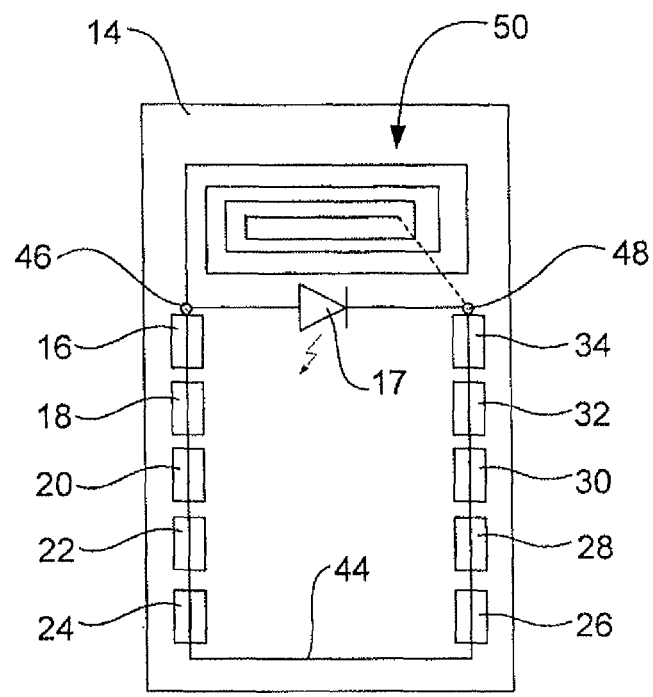
FIG. 4 is a more detailed diagram depicting a tag forming part of the system depicted in FIG. 2.

A more detailed representation of the interrogator 12 and a tag 14 is shown in FIGS. 3 and 4. The interrogator 12 and tag 14 are described in greater depth in International Patent Application PCT/AU2008/001293, to the present Applicant, the entire contents of which are incorporated herein by reference. The tag 14 includes a plurality of micromechanical vibratable members 16 to 34 each having a particular resonant frequency. A common electrical conductor 44 runs along or through the vibratable members and extends beyond the vibratable members to electrical terminals 46 and 48. A coil antenna 50 interconnect the terminals 46 and 48. The vibratable members 16 to 42, the electrical conductor 44, the electrical terminals 46 and 48 and the coil antenna 50 may be formed on a dielectric or semi-conductor substrate. An LED 17 or other light emitter may be connected across the coil antenna 50 in order to provide a visual indication that an excitation signal is being applied to the coil antenna.

The vibratable members 16 to 34 are caused to vibrate by an applied excitation or interrogation signal generated by the interrogator 12 that induces an alternating current in the electrical conductor 44 by means of Faraday induction via the coil antenna 50. The exemplary vibratable members 16 to 34 are described in International Patent Application WO 2004/084131, to the present Applicant, the entire context of which are incorporated herein by reference.

In one exemplary embodiment, the vibratable members 16 to 34 are vibratable by a Lorentz force. The Lorentz force is the force that acts on a charged particle travelling through an orthogonal magnetic field. In this instance, a magnetic field is applied to the vibratable members 16 to 42 in a direction perpendicular to the current flow through the electrical conductor 44.

Figure 5:
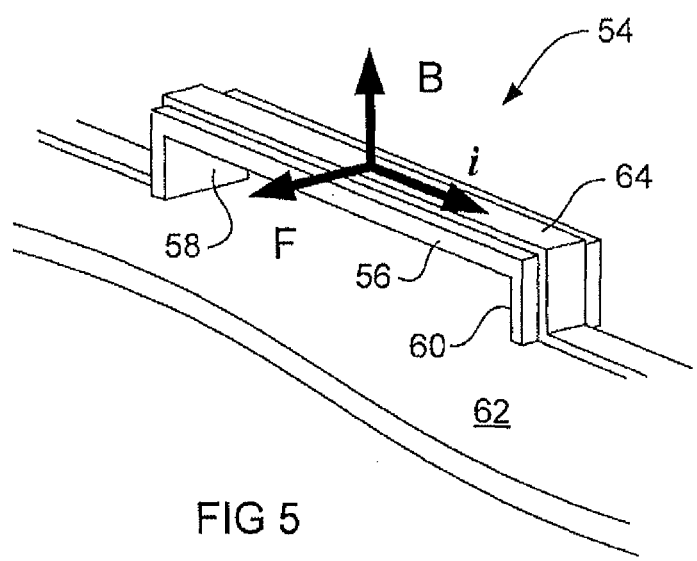
FIGS. 5 and 6 are isometric views of two different embodiments of a vibratable member forming part of the tag shown in FIG. 4.

FIG. 5 depicts an exemplary vibratable member in the form of a bridge structure 54 including a beam 56 supported by two columns 58 and 60 projecting from a substrate 62. The structure shown in FIG. 5 may be formed by conventional semiconductor fabrication techniques involving the use of known etching and electro-deposition processes. Once the bridge structure 54 has been formed on the substrate 62, an electrically conductive path 64 is then electro-deposited along the length of the structure 54. The electrically conductive path 64 forms part of the conductor 44 shown in FIG. 4.

When an interrogation signal is applied to the tag 14, alternating electrical current is induced in the antenna coil 50 which thus causes the flow of electrical current through the conductive path 64. In the presence of an orthogonal magnetic field, a force is then applied to the beam 56 in a direction that is orthogonal to both the direction of current flow and the magnetic field direction. Since the current in the conductor 64 is an alternating current, the orthogonal force generated is also an alternating force, resulting in the vibration of the beam 56. If the frequency of the alternating current in the conductor 64 is at or near the resonant frequency of the beam 56, the beam 56 will vibrate.

Figure 6:
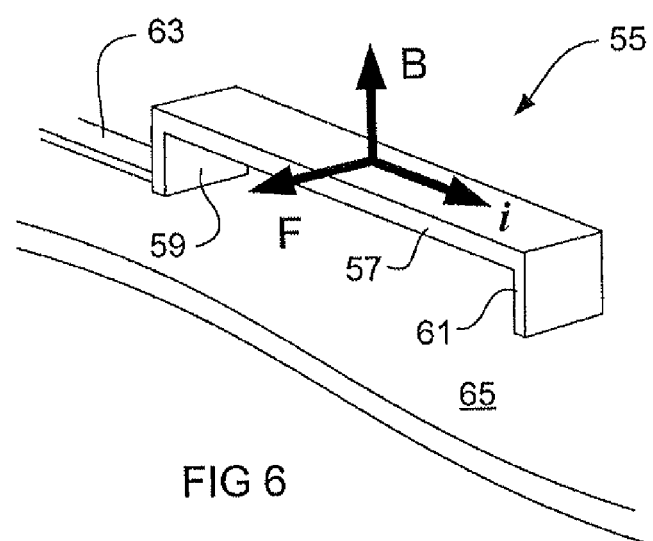

Another exemplary vibratable member is shown in FIG. 6. In this case, the vibratable member is in the form or a bridge structure 55 including a beam 57 supported by two columns 59 and 61. Unlike the embodiment depicted in FIG. 5 though, the beam 57 is formed from the same material as the electrically conductive path 63 supporting the two columns 59 and 61. The structure shown in FIG. 6 may be formed by conventional semi-conductor fabrication techniques involving the use of known etching and electro-deposition processes. Typically, the electrically conductive path 63, columns 59 and 61 and mean 57 are deposited on the substrate 65 in the same deposition step(s).

Returning once again the FIG. 3, the interrogator 12 includes a microcomputer 70, an Inverse Fast Fourier Transform (IFFT) block 72, a up-conversion/interpolation section 74, a digital to analogue converter 76, an analogue transmitter section 78, an interrogator coil antenna 80, an analogue receiver section 82, a down-conversion/decimation section 84, a quadrature partial band local oscillator 86 and a Fast Fourier Transform (FFT) block 88. In this embodiment, the IFFT block 72, up-conversion/interpolation section 74, down-conversion/decimation section 84, quadrature partial band local oscillator 86 and Fast Fourier Transform (FFT) block 88 are implemented in hardware using a Field Programmable Gate Array (FPGA) device 71.

The interrogator 12 furthermore includes a magnetic field generator 150 for generating the required magnetic field depicted in FIG. 3. The magnetic field generator 150 may be implemented in a number of ways, for example, by use of one or more electromagnets or permanent magnets. In this example, operation of the magnetic field generator 150 is controlled by the microcomputer 70. The microcomputer 70 includes a conventional central processing unit 90 with associated volatile memory 92 and non-volatile memory 94. Both memories 92 and 94 are used for the storage of programs and data.

The partial band up-conversion/interpolation section 74 includes memory devices 96 and 98 which respectively store data corresponding to the imaginary and real components of a frequency domain spectral synthesis of a narrow band signal having a half sinusoidal shape. Frequency-domain data is firstly transferred from the microcomputer 70 to the memory devices 96 and 98. The IFFT block 72 then performs an inverse Fast Fourier Transform on the data stored in the memory devices 96 and 98 so that the data is transformed from the frequency domain into the time domain. The partial band up-conversion/interpolation section 74 further includes Finite Impulse Response (FIR) interpolation filters 100 and 102 respectively connected to outputs of the memory devices 96 and 98. The FIR interpolation filters act to up-sample the data stored in the memory devices 96 and 98, thereby minimising the data required to be stored in those memory devices as well as improving the accuracy of computations subsequently performed in the interrogator 12. The up-conversion/ interpolation section 74 pass-band bandwidth is sufficient to admit the partial-band bandwidth.

The interrogator 12 further includes a quadrature Direct Digital Synthesiser (DDS) partial-band local oscillator 86. The DDS partial-band local oscillator 86 includes a look-up table 200 for storing the amplitude of a sinusoidal waveform at a series of discrete phase angles. An accumulator, consisting of a summation device 202 and an M-bit phase register 204, steps between consecutive phase angles at a frequency determined by an M-bit phase increment 206. Accordingly, the DDS partial-band local oscillator 86 acts to read values in the look-up table 200 and thereby generate a digital representation of the cosine of a time varying signal at a desired partial-band centre frequency. An offset block 208 enables the simultaneous reading of values in the look-up table 200 of a digital representation of the minus sine of that a time varying signal.

The partial band up-conversion/interpolation section 74 includes multipliers 104 and 106. The multiplier 104 acts to multiply the interpolated time domain imaginary component of the narrow band signal spectral synthesis with the time varying minus sine function produced by the quadrature partial band local oscillator 86. Similarly, the multiplier 106 acts to multiply the real component of the narrow band signal spectral synthesis at the output of the FIR interpolation filter 102 by the time varying cosine function generated by the quadrature partial band local oscillator 86.

The outputs from the two multipliers 104 and 106 are added and then provided as an input to the digital to analogue converter 76. The signal resulting from this addition corresponds to a time domain representation of the real part only of a complex signal having a frequency spectrum of a half sinusoidal shape which is centred at a desired partial-band centre frequency determined by the local oscillator 86. The output of the digital to analogue converter 76 is supplied to the analogue transmitter block 78, which includes a low pass filter 110 and Radio Frequency (RF) power amplifier 112. When a transmission switch 114 forming part of the analogue transmitter strip is switched to a transmit position, a "ring-up" signal at the output of the RF power amplifier 112 is supplied to the interrogator coil antenna 80. A corresponding signal is generated in the antenna coil 50 of the tag 14 by transformer action. In this embodiment, this transmission switch is implemented using MOSFETs.

It is desirable to include a series-resonance capacitance in series with the interrogator antenna coil 80 and the RF power amplifier 112 in order to ensure a maximal current flow in the antenna coil 80, given that the maximum output voltage of the RF power amplifier 112 is generally limited to a maximum value. It is also desirable that a consistent level of current is induced in the coil antenna 50 of the tag, across the range of frequencies within which ring-up signals may be applied. To this end it may be necessary to alter the value of the capacitance in series with the interrogator antenna coil 80 as the interrogation process steps through the sequence of partial bands. This capability for altering capacitance is shown in FIG. 1 by a capacitor bank 152 including capacitors $C_1$, $C_2 \ldots C_n$. Each of the capacitors $C_1, C_2 \ldots C_n$ is connectable in series with the antenna coil 80 by selective operation of tuning MOSFETs 154, 156 and 158 controlled by the microcomputer 70. An additional optional capacitor $C_0$ serves to set the maximum tuning frequency of this array in the operating situation where all MOSFETs are biased off.

Since the voltages at the drains of the tuning MOSFETs 154, 156 are generally much higher than that present at the output of the RF power amplifier, by virtue of the resonant magnification of $C_0, C_1, C_2 \ldots C_n$ in conjunction with the antenna coil 80, a DC bias supply of sufficient magnitude is required. In FIG. 3, the MOSFETs 145, 156 are illustrated as N-channel devices, so this DC bias supply should have a positive voltage with respect to the sources of the MOSFETs. However the a configuration using P-channel MOSFETs is equally valid, however the DC bias supply voltage should have a negative value with respect to the sources of the MOSFETs. This DC bias value is chosen so as to ensure that any given MOSFETs in an off state always has a positive voltage on its drain terminal. Parasitic conduction though this MOSFETs body-diode is thereby avoided in operation. The DC bias is conveyed to the drains of the MOSFETs by suitable resistors $R_1$ to $R_n$.

After each ring-up signal is applied to the tag 14, and then subsequently removed, an electrical response will appear across the coil antenna 50 due to contributions from resonances in the tag 14 which absorbed energy during the ring-up signal. This electrical response or "ring-down" signal is transferred to antenna 80 by transformer action and applied to the input of the analogue receiver block 82.

The analogue receiver section 82 includes a receiver front end switch 116, an RF low noise amplifier 118, band pass filter 120, adjustable RF gain strip 122, high pass filter 124 and low pass filter 126. The various elements forming part of the analogue receiver at step 82 act to condition the ring-down signal before application to an analogue to digital converter 128. After digitisation by the analogue to digital converter 128, the ring-down signal is then down-converted and decimated by the partial band down-conversion/decimation section 84. Accordingly, the digitised ring-down signal at the output of the analogue to digital converter 128 is applied to the input of multipliers 130 and 132 for multiplying respectively with the digitised cosine function and digitised negative sine function generated by the local oscillator 86.

The outputs of the multipliers 130 and 132 correspond to time domain digital representations of the real and imaginary components of the down-converted ring-down signal. The partial band down-conversion/decimation section 84 includes FIR filters followed by decimators 134 and 136, respectively connected to the outputs of multipliers 130 and 132. The FIR decimation filters 134 and 136 act to down sample the digitised signals received from the outputs of the multipliers 130 and 132. The partial band down-conversion/decimation section 84 further includes memory devices 138 and 140 for storing the down-sampled digitised data received from the outputs of the FIR decimation filters 134 and 136. Summation devices 142 and 144 are respectively connected between the FIR decimation filter 134 and memory device 138, and the FIR decimation filter 136 and the memory device 140 so that the real and imaginary component of a number of digitised and down converted ring-down signals can be summed (for purposes of averaging) in the memory devices 138 and 140. The down-conversion/decimation section 84 pass-band bandwidth is also sufficient to admit the partial-band bandwidth.

The digitised time domain data stored in the memory devices 138 and 140 is forwarded to the FFT block 88 for transformation into the frequency domain. The microcomputer can then collect the frequency-domain data from this memory. This data, namely ring-down signals averaged over one or more ring-up/ring-down cycles is then analysed by the microcomputer to identify resonances from the tag 14.

Figure 7:
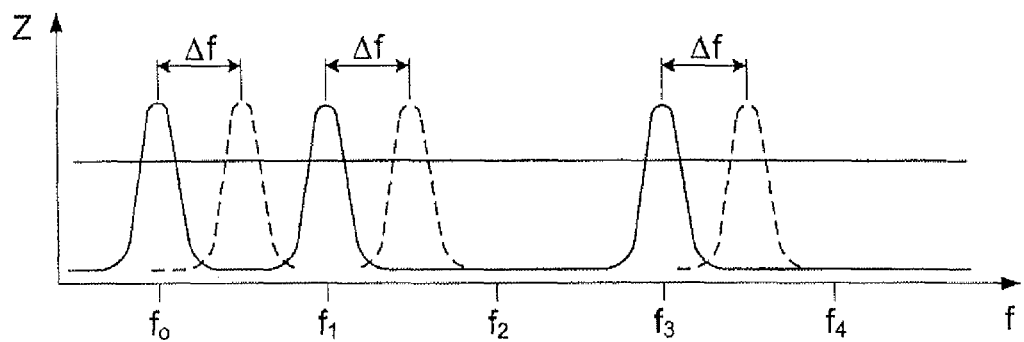
FIG. 7 is a graphical representation of the frequency of response of the tag shown in FIG. 4, depicting notably a shift in resonant frequency of the vibratable members of the tag as a function of temperature.

Referring now to FIG. 7, each of the resonant members forming part of the exemplary tag 14 have a notional resonant frequency corresponding to one of a predetermined number of resonance frequencies $f_0, f_1, f_2, f_3$ etc. If the interrogator detects a resonant frequency at any of the frequency positions $f_0$ onwards, the microcomputer 70 interprets that resonance frequency as a binary "1". By contrast, the absence of a resonant frequency at any of those predetermined frequency positions is interpreted as a binary "0". The sequence of binary 1s and 0s detected by the microcomputer 70 corresponded to a tag identification code. Use of tags including a plurality of micromechanical vibratable members of this type are ideally suited to use in temperature controlled environments for storing biological samples, and in particular those environments in which extreme temperature conditions are experience, such as those associated with liquid nitrogen. Unlike conventional semi-conductor electronics, such micromechanical resonant members continue to resonate and the associated tag continues to function even at such extreme temperatures.

Figure 8:
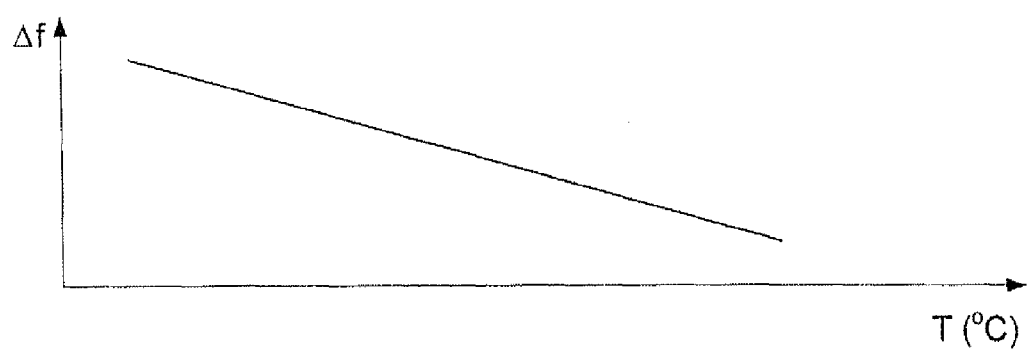
FIG. 8 is a graphical depiction of the function between that shift in resonant frequency and temperature.

Although each of the resonant members are assigned a notional resonance frequency at one of the predetermined frequency positions $f_0$ onwards, the exact resonant frequency of each vibratable member will vary as a function of the temperature to which the vibratable members is exposed. In the example shown in FIG. 8, the shift $\Delta f$ in resonant frequency of the vibratable members varies linearly as a function of temperature. In other embodiments of the invention though, vibratable members having other reproducible and reliable temperature profiles may be used.

This correspondence between shift in resonant frequency and temperature is used by the system depicted in FIG. 2 in order to monitor the thermal history of the group of one or more samples associated with each tag. Advantageously, taking advantage of this temperature dependent characteristic of the resonant members forming part of each tag enables the identification code encoded in each tag as well as the temperature experienced by each tag to be read by the interrogator without requiring any additional components or elements, since the shift in resonant frequency is an inherent property of the vibratable members of the tag.

Figure 9:
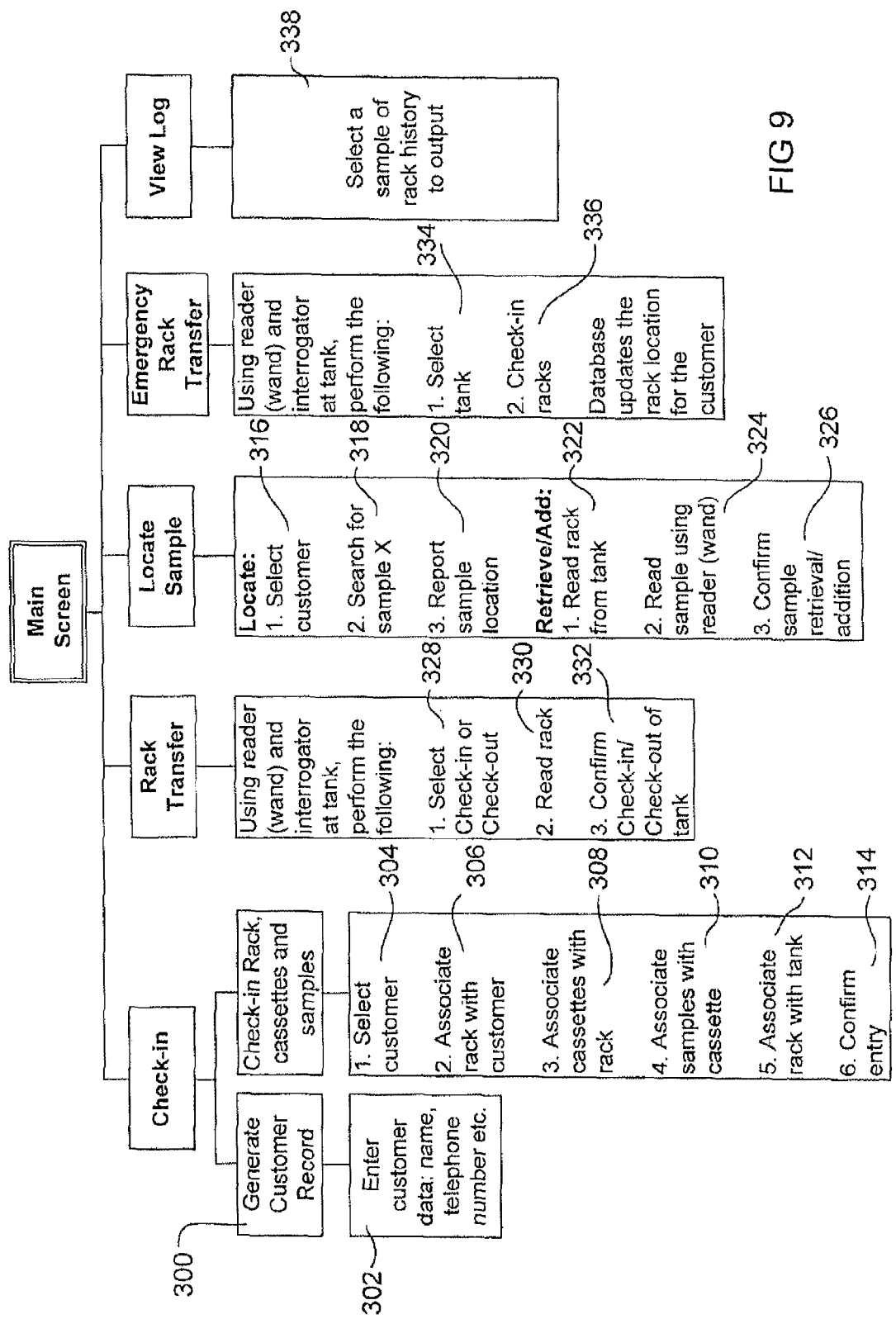
FIG. 9 is a schematic representation of the functionality provided by the system depicted in FIG. 2 as controlled by the controller forming part of the system depicted in FIG. 2.

FIG. 9 depicts a series of different processes able to be implemented by the system shown in FIG. 2 during the storage and monitoring of biological samples in the cryogenic tanks 210 to 206. Each of these processes are enabled via the controller 236 via the display 240 and data/command input device 242. In a first "check-in" process a customer record is initially generated at step 300 and, at step 302, customer data such as the customer's name, telephone number and other personal details are entered.

Having firstly created a customer record, the location of biological samples associated with that customer in the cryogenic tank is then recorded. At step 304, the desired customer record is selected. At step 306, a particular rack is selected for association with that customer and at steps 308 and 310 a cassette and sample bags associated with that cassette are selected. At step 312 that rack is then associated with a particular cryogenic tank. Finally, at step 314, the data entered is confirmed.

When it is desired to locate a particular customer's biological sample, an operator firstly selects the desired customer at step 316, and at step 318 searches for the desired sample. Corresponding data is then retrieved from the database 238 and the location of that particular sample is displayed to the operator on the display 240. If retrieval of that sample is then required, the tank in which that sample is firstly located and the lid on that tank is then opened.

The wand 244 forming part of the interrogator 12 is then used to read the tag affixed to each of the racks stored within that cryogenic tank, at step 322 until the desired rack is located. At this point, the wand may be mechanically coupled to the rack 208 in order to continually read information from the tags within that rack, at step 324. In other embodiments, mechanical coupling may not be required and the same continual reading may be achieved, for example, by an operator maintaining the wand sufficiently proximate the rack for a read operation to take place. A switching mechanism may be employed in order for the excitation signal generated by the coil 254 of the wand to be sequentially applied to each of the rack slot coils 258 to 264 in order that the tags associated with a group of one or more samples are read in turn.

In this way, while the desired customer sample is being located and removed from the rack for use, a thermal history of the remaining biological samples in the rack is able to be constructed by continually reading the ambient temperature to which the rack 208 is subjected. The thermal history is completed when the rack 208 is positioned within the cryogenic tank 200, and the wand removed, by data from a temperature sensor 270 within the cryogenic tank and connected to the central controller 236. Once the sample has been located and retrieved, the rack is then returned to the cryogenic tank and, at step 326, an operator confirms that the sample has been retrieved.

A similar process is followed when, rather than retrieving a biological sample from a cryogenic tank, it is desired to add a biological sample.

It may also be desirable to transfer a rack from one cryogenic tank to another without adding or removing biological samples. In this case, an operator selects, at step 328 a "check-in" or "check-out" process, and then uses the wand 244 to identify a desired rack within a particular cryogenic tank, at step 330. The wand may once again be mechanically coupled to the rack in question so that during transfer of the rack from one cryogenic tank to the other a thermal history of biological samples stored within that rack can be maintained. Once the rack transfer procedure has been terminated, then an operator confirms termination of the process at step 332. It may be desirable under emergency circumstances, to perform an emergency rack transfer from one cryogenic tank to another. This typically occurs when the temperature controllable chrematistics of the cryogenic tank are no longer functioning so that it is desirable to transfer all that is maintained within that cryogenic tank to other temperature controlled environments.

In this situation, a particular is selected, at step 334 as experiencing an emergency condition, and the tank to which a particular rack is to be transferred is selected. At step 336 the racks are transferred, but on this occasion without coupling the wand to each rack prior to and during transfer. In emergency situations speed is of the essence and it is more desirable to rapidly transfer the racks from one tank to another rather than to maintain a precise thermal history of the biological samples in those racks. At step 336, the racks are checked into their new locations in the cryogenic tanks that were not subject to the emergency failure, and the position of the racks and their cassettes and sample bags housed within are then updated in the database 238. The database 238 nevertheless records that an emergency rack transfer procedure has occurred during the thermal life of the biological samples within the transferred racks.

The central controller, display and data/command input device also enable a log to be viewed, at step 338 of a particular biological sample in order that its thermal history can be retrieved.

Figure 10:
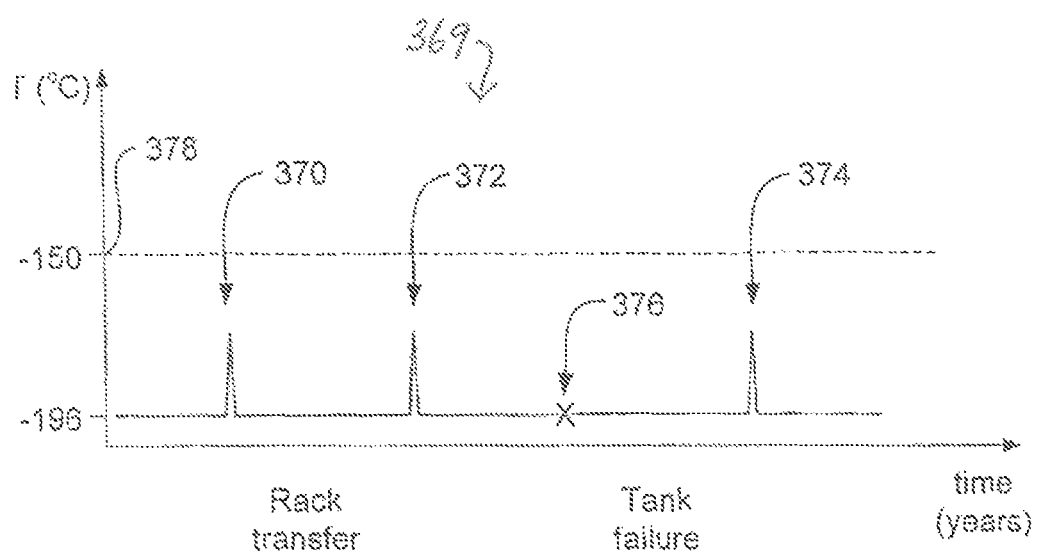
FIG. 10 is a graphical depiction of an exemplary thermal history of a biological sample stored and monitored by the system shown in FIG. 2.

FIG. 10 depicts an exemplary log for a group of one or more samples associated with a particular tag forming part of the system depicted in FIG. 2. In this exemplary thermal history 369, rack transfer events, resulting in temporal spikes in the temperature experienced by a particular biological sample are referenced 370, 372 and 374. An emergency rack transfer procedure was initiated during the life of the biological samples, and is referenced 376 in FIG. 13. It will be noted that during the standard rack transfer procedures, the temperature at which the particular rack was exposed was nevertheless recorded, but did not exceed an alarm-triggering temperature 378. However, during the emergency rack transfer procedure, the temperature was not recorded. The temperature limit 378 may be stored in the database 238 and accessed by the central controller 236 in order for an alarm-triggering condition to be detected.

As has been previously explained, the interrogator 12 includes signal processing circuitry (in the interrogator body 246), and a reading head or wand 244 in communication with the signal processing circuitry. The reading head 244 includes an interrogation coil 254, and the signal processing circuitry is configured to generate an interrogation signal in the interrogation coil. Each machine readable tag, such as the tag 14 depicted in FIG. 4, includes an antenna coil 50 coupled to resonant members 16 to 34. When the interrogation is positioned proximate the antenna coil, an excitation signal is induced in the antenna coil from the interrogation signal in the interrogation coil.

Figure 11:
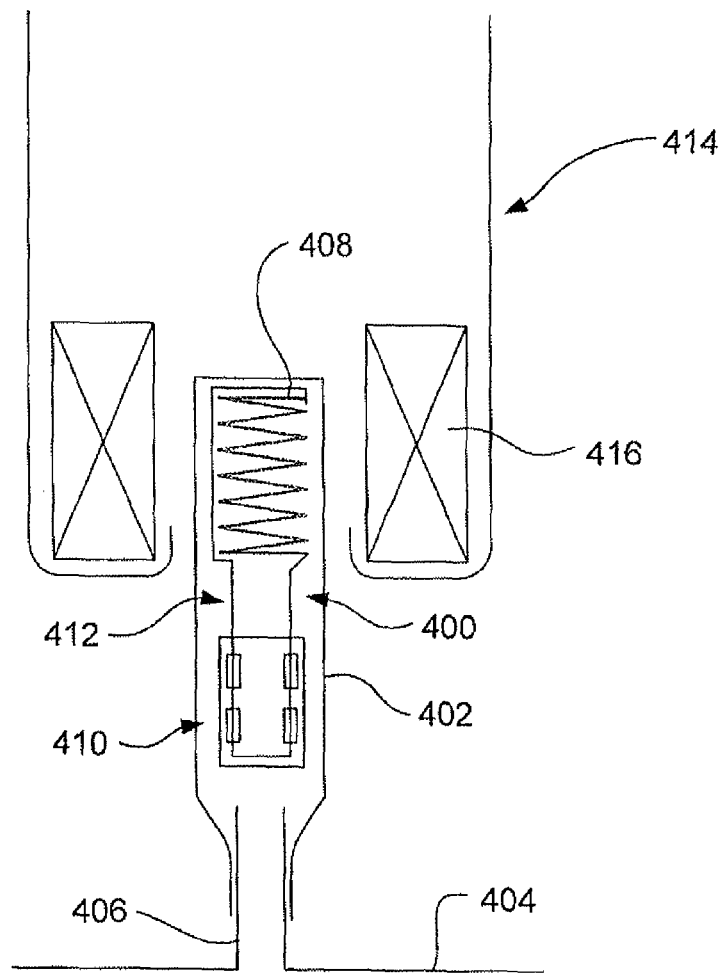
FIG. 11 is a schematic diagram of a machine readable tag and interrogator reader head forming part of the system a system for storing and monitoring samples in accordance with a second embodiment of the present invention.

FIG. 11 depicts one embodiment of a machine readable tag and reading head which is particularly suited for use with applications involving the storage of blood plasma, cord blood, stem cells and other biological materials in bags for storage in a cryogenic tank or other similar freezer or low temperature environment. As shown in this figure, the machine readable tag 400 is housed within a sleeve 402 adapted for attachment to a storage bag 404. In particular, the storage bag 404 includes a port 406 for introducing biological samples into the bag. The port 406 projects from the bag 404 and provides a convenient location to which the machine readable tag 400 may be attached by means of the sleeve 402. In this embodiment, the sleeve 402 is placed around the port 406 and is affixed thereto by any suitable means. The machine readable tag 400 and sleeve 402 could also be attached to a projection extending from a storage tank, freezer, rack, container or other storage element forming part of a sample storage system. It will be appreciated that the attachment of a sleeve to a port or other projection may be substituted by another means for attaching the machine readable tag, in other embodiments.

Conveniently, the sleeve 402 may be formed from a plastic or light material which shrinks upon the application of heat so that once the sleeve 402 is placed over the port 406, the application of heat will serve to locally shrink the sleeve around the port and affix the machine readable tag 400 to the bag 404. It will be appreciated that whilst a port is a projection which exists in bags used for the storage of biological samples, and is therefore an existing and convenient attachment point form machine readable tags, in other embodiments of the invention other projections may be provided to which the sleeve 402 may be attached.

The machine readable tag 400 includes an antenna coil 408 connected to a plurality of resonant members 410 by means of conductors 412. The antenna coil 408 has a helical form. The reading head 414 is in the form of a tube housing a coil 416, which also has a helical form, at its tip. The helical coil 416 has a larger diameter than does the helical coil 408, and the antenna coil 408 is adapted to be located within the interrogation coil 416 during tag reading. In other embodiments of the invention, the interrogation coil may have a smaller diameter than that of the antenna coil, so that the interrogation coil can be inserted into the antenna coil during tag reading. As can be seen in FIG. 11, the antenna coil and interrogation coil are concentrically located in the depicted tag reading position. In this way, inductive coupling between the interrogation coil 416 and the antenna coil 408 is optimised. Moreover, this coil alignment method mitigates against any misalignment error that may occur between two planar coils. A further representation of the bag 404, reading head or wand 414, sleeve 402 encasing the machine readable tag 412 and port 406 is shown in FIG. 12.

Figure 12:
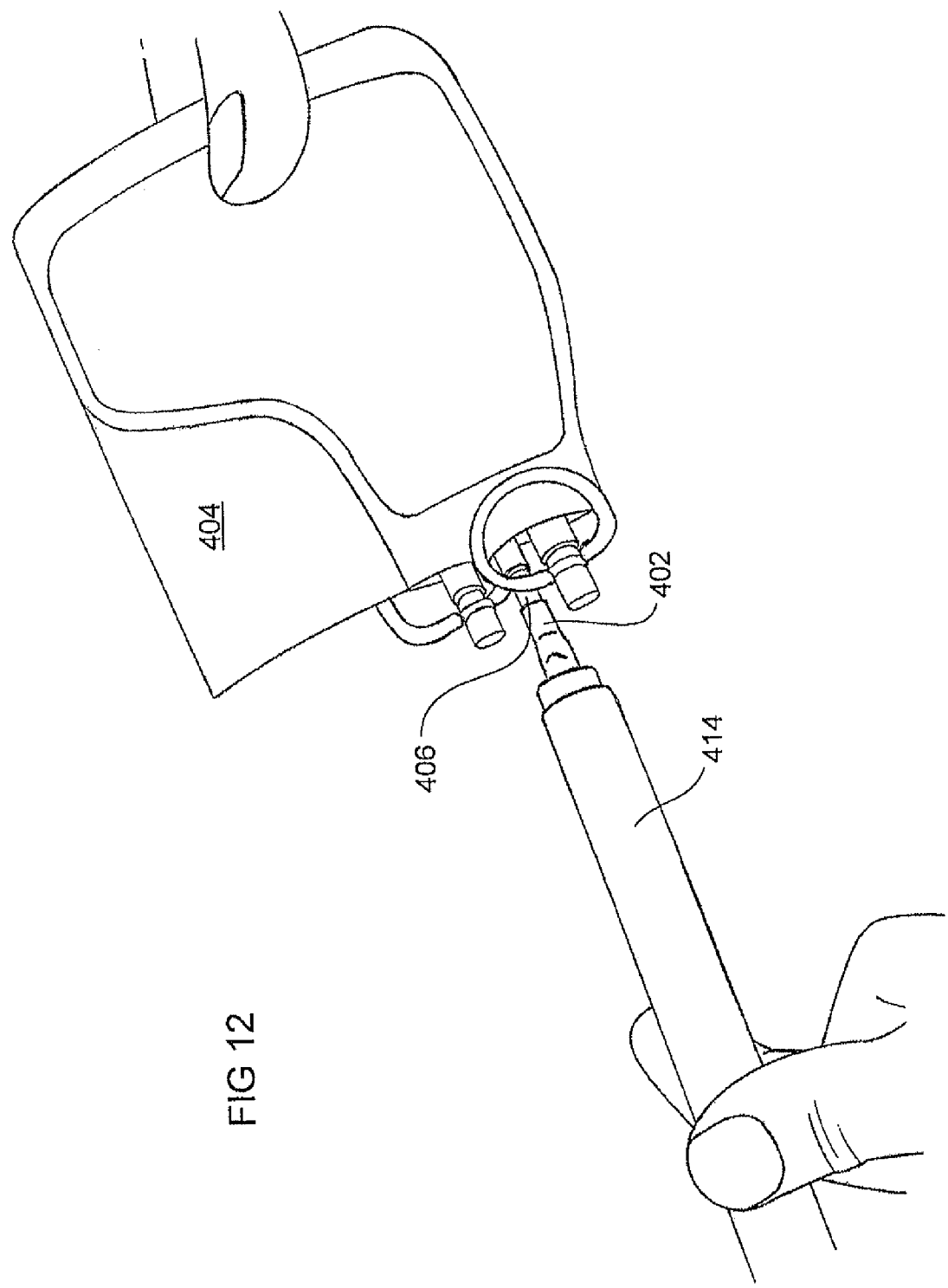
FIG. 12 is more detailed view showing the reading of the machine readable tag shown in FIG. 11 when attached to a sample storage bag.
Figure 13:
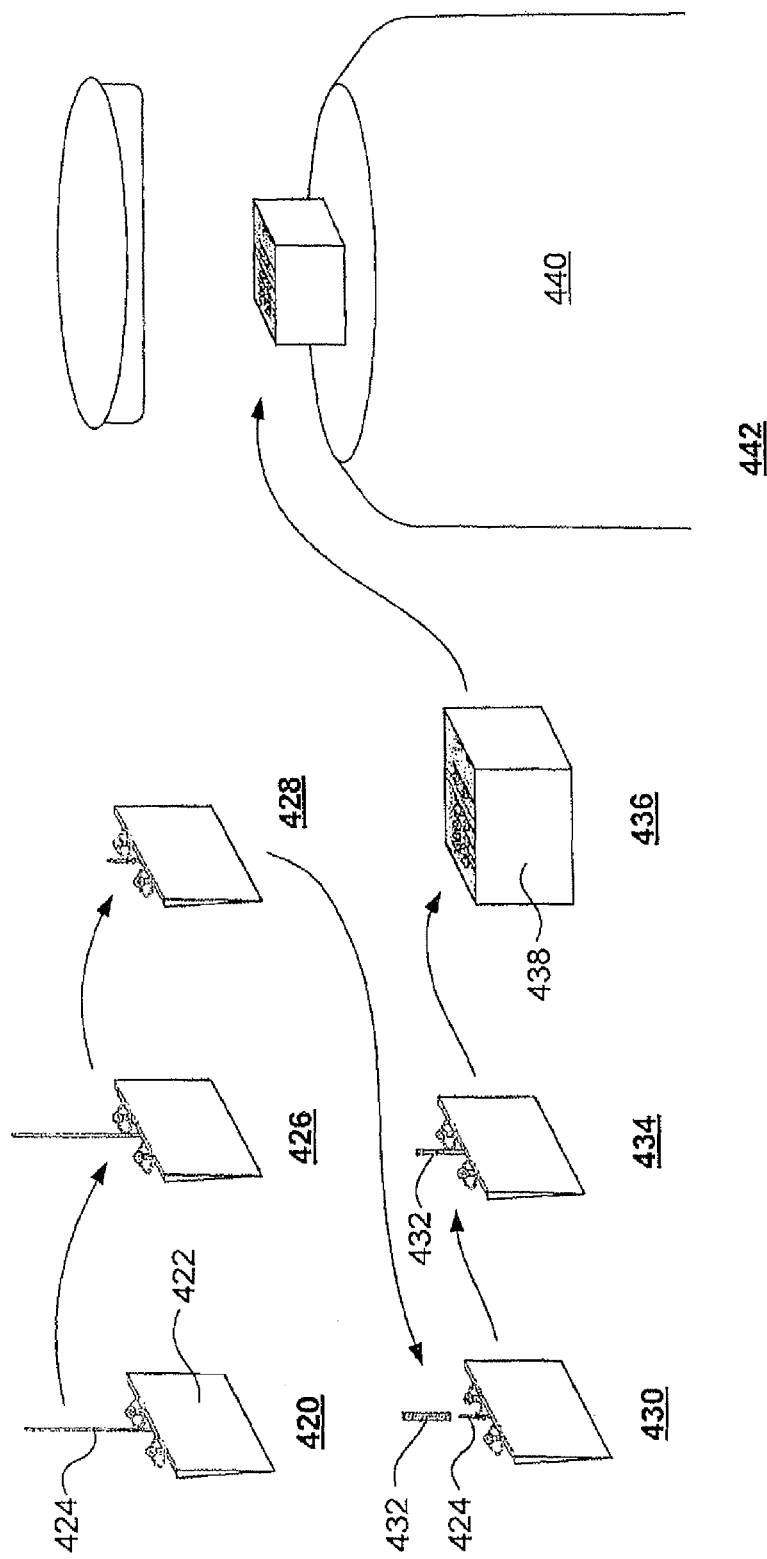
FIG. 13 depicts a sequence of steps showing the manner in which samples can be stored within the sample storage bag shown in FIG. 12 via a port, and how a machine readable tag may be affixed to the bag and placed in a temperature controlled environment.

FIG. 13 depicts a sequence of steps showing the manner in which blood plasma or other biological materials may be housed within a bag such as that depicted in FIGS. 11 and 12 via a port, and how a machine readable tag such as that depicted in those same figures may be affixed to the bag and placed in a temperature controlled environment. Step 420 depicts a blood plasma storage bag 422 including a port 424 projecting therefrom. Blood plasma is added to the interior of the bag via the port 424, as depicted in step 426. Excess tubing is then removed from the port 424 by use of a head clamp as shown in step 428. At step 430, a sleeve 432, of the type described in relation to FIGS. 11 and 12 and encasing a machine readable tag, is placed over the end of the cut port 424. The sleeve 432 is secured to the port 424 by means of a heat gun, as shown in step 434, so that a localised portion of the sleeve is secured about the port. Having thus tagged the bag 422, at step 436 the bag is placed inside a box 438 or other support structure or object and then placed within a freezer 440 or other structure defining a temperature controlled storage environment as shown in step 442.

Figure 14:
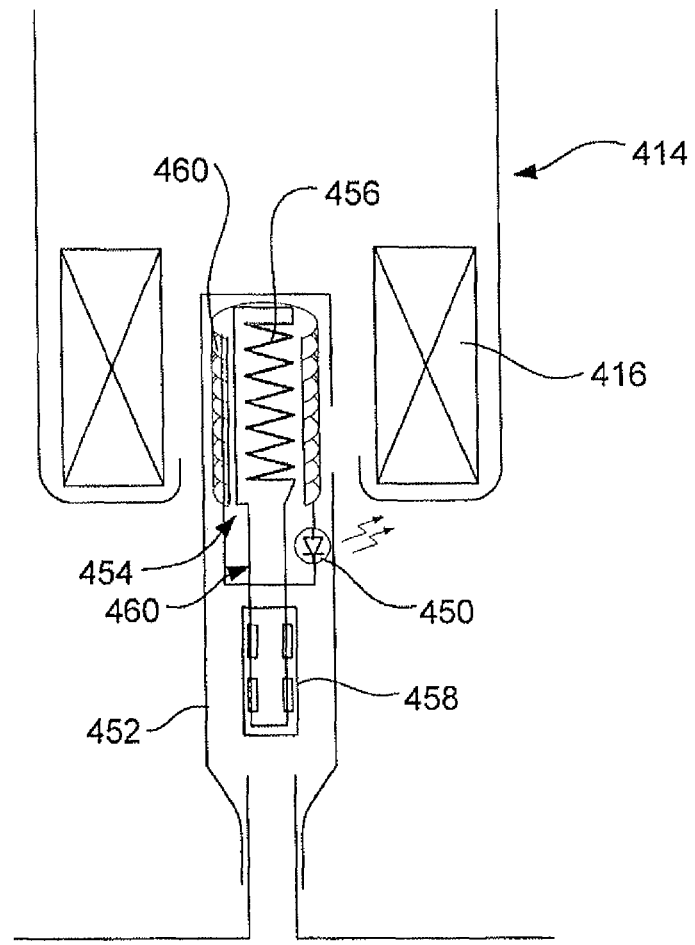
FIG. 14 is a schematic diagram of a first variation to the machine readable tag shown in FIG. 11.

In a variation depicted in FIG. 14, the machine readable tag further includes a light emitting diode (LED) or other light emitting device 450. The LED may be located so as to be visible through the sleeve 452 encasing the machine readable tag 454. As was described in relation to FIGS. 11 and 12, the machine readable tag 454 includes an antenna coil 456 coupled to a plurality of resonant members 458 by means of conductors 460. In addition however, the sleeve 452 encases a second antenna coil 460 coupled to and adapted to drive the LED 450. The antenna coil 460, in this embodiment, is mounted concentrically with the antenna coil 456 and one of the antenna coil 456 and antenna coil 460 is housed within the other, so that current is induced in both the first and second antenna coils 456 and 460 during a tag read operation, in which current is induced in both antenna coils. In this manner, the antenna coil 460 and LED 450 to which it is coupled provide a positive visual indicator to an operator that the machine readable tag is being read. This is particularly useful in low temperature storage environments which are typically foggy and difficult for the operator to visually confirm that a correct tag read operation has occurred.

With a LED 450 on a separate circuit to the machine readable tag, and a suitably chosen resistance in series with the LED 450 and the antenna coil, the following identification process can be achieved. Firstly, the reader head acts to read the tag identification code with a lower power current. The interrogator then looks up on a database to check if this is the identification code is currently being searched. If the identification code matches the identification code being search searched, a larger current is transmitted to the interrogator coil, causing illumination of the LED and giving the user feedback about a successful identification.

This process can be applied to not only the memory device but to an RFID tag in combination with a LED or other visual indicator. A frequency selective circuit could also be used in the LED and coil tag circuit, whereby the interrogator emits a signal at a different frequency that that which the tag responds, and activates the LED to light.

In the arrangements depicted in FIGS. 11 to 14, the machine readable tag is affixed to a port projecting from the exterior of a sample storage bag. However, in other embodiments of the invention, the resonant members may be positioned inside the bag or other container, so as to provide a more accurate indication of the temperature of the sample stored within the bag.

Figure 15:
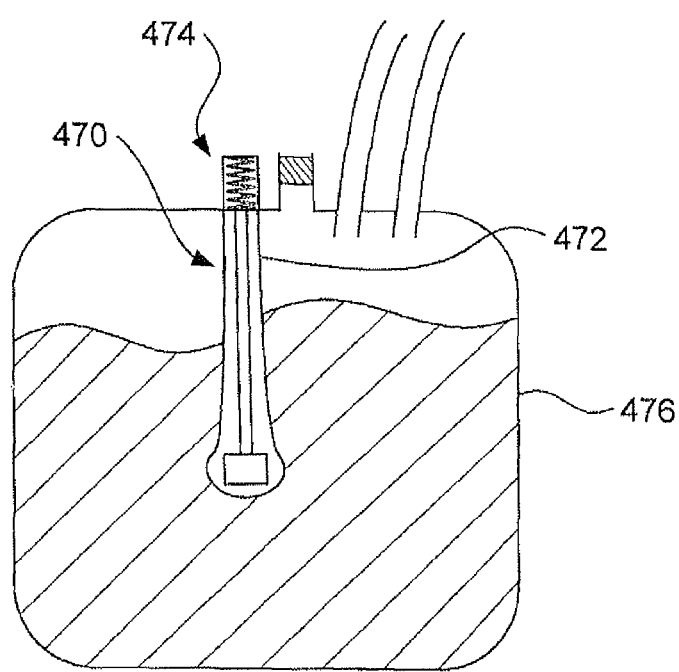
FIGS. 15 and 16 are schematic diagrams of a second variation to the machine readable tag shown in FIG. 11.
Figure 16:
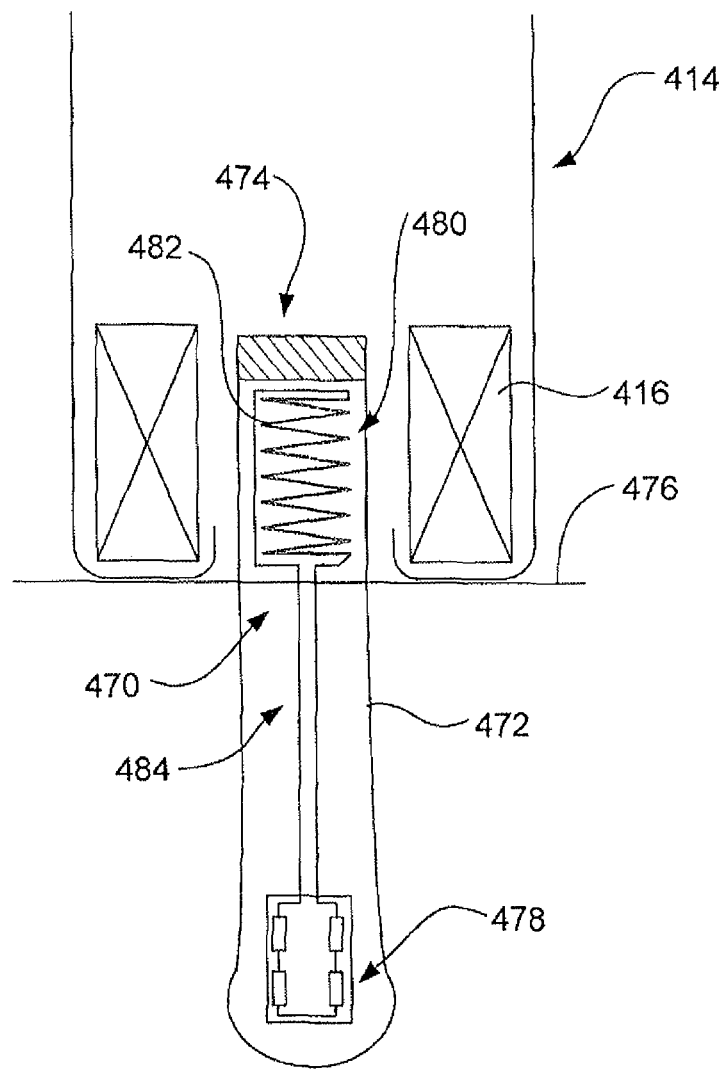

As shown in FIGS. 15 and 16, an elongate machine readable tag 470 is inserted in a sleeve 472 projecting from a port 474 to the interior of the bag 476. In this case, the machine readable tag 470 includes a first portion 478 locatable inside the container (within the sleeve 472), a second portion 480 housing an excitation coil 482 and affixed to the bag 476 so as to project from the exterior of the bag to enable the induction of current in the excitation coil 482 by the reading head 414. The machine readable tag 470 further includes a third elongate portion 484, interconnecting the first and second portions of the machine readable tag, and configured to position the plurality of resonant members inside the container when the excitation coil projects from the exterior of the container.

Figure 17:
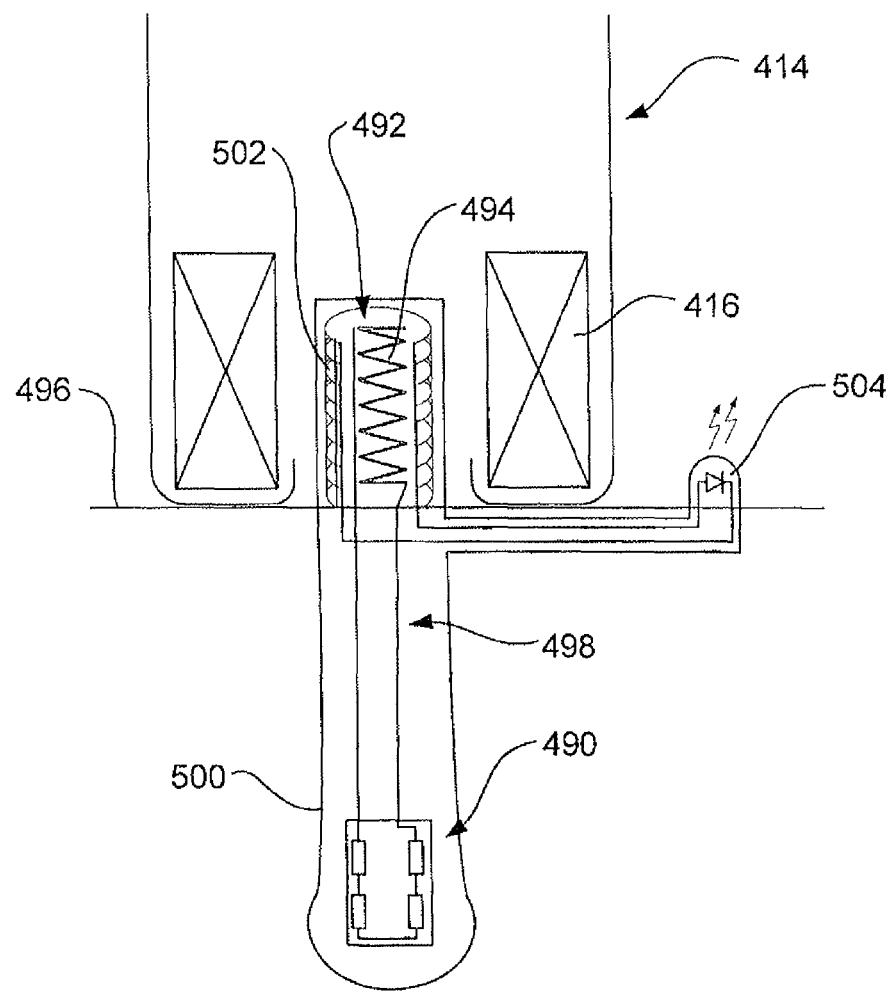
FIG. 17 is a schematic diagram of a third variation to the machine readable tag shown in FIG. 11.

FIG. 17 depicts a variant of the machine readable tag depicted in FIGS. 15 and 16. In addition to a first tag portion 490 housing a plurality of resonant members, a second tag portion 492 housing the excitation coil 494 so that the coil projects from the exterior of a bag 496, and a third elongate portion 498 interconnecting the first and second portions, so that the first portion can be located inside the bag 496 within a sleeve 500, the machine readable tag further includes a second antenna coil 502 connected to an LED or other light emitting device 504 mounted within the bag 496 so as to be visible through a window. As was the case in relation to the embodiment described in FIG. 14, one of the antenna coils is mounted within the other and current is induced in both during a tag read operation, so that a visual indication of a successful tag read operation is provided to an operator via the light emitting device 504.

In the embodiments shown in FIGS. 16 and 17, the machine readable tag is not secured to the bag by means of a sleeve placed over a port. Rather, the machine readable tag is placed inside a port. A sterile heat sealer is then used to seal the end of the port and thus enclose the tag in the sleeve formed within the bag.

Whilst the storing and monitoring samples depicted in FIG. 2 included a series of interconnected rack excitation coils adapted to use current in antenna coils of machine readable tags located or housed anywhere within a single rack stored within the cryogenic tank 200 in a single read operation, in other embodiments of the invention, a separate read operation may be required to read each machine readable tag.

Figure 18:
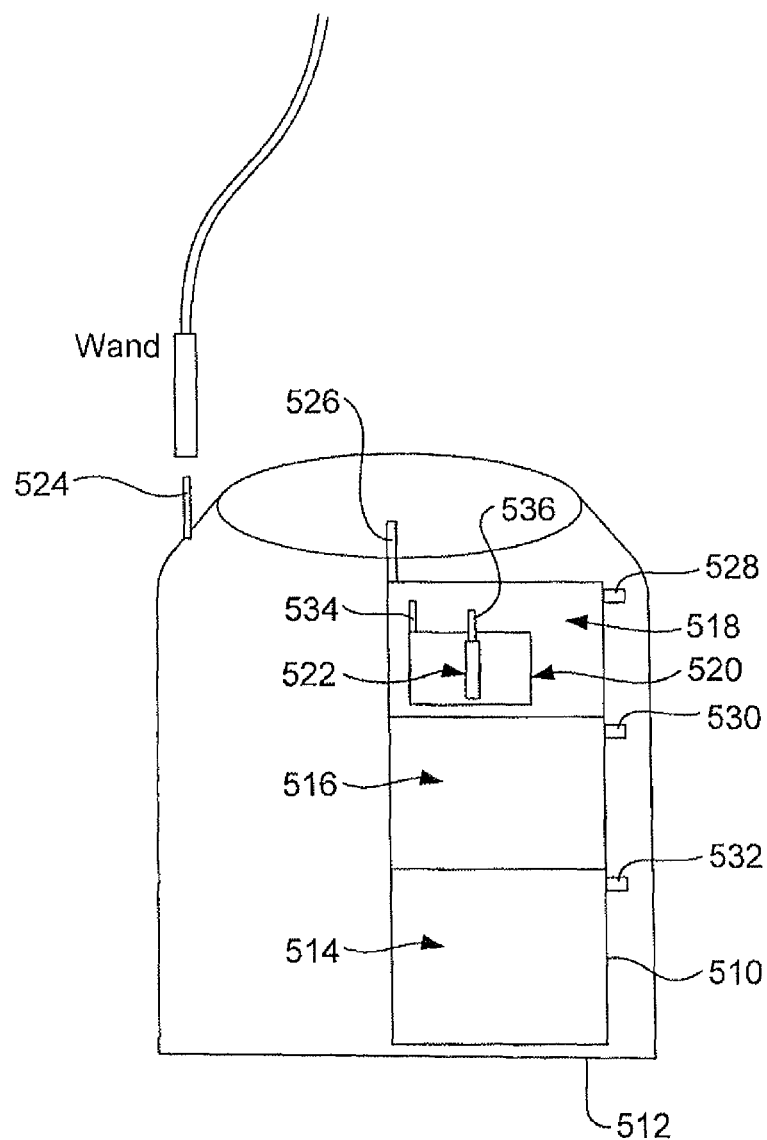
FIG. 18 is a schematic diagram depicting some elements of an alternative temperature-controlled environment to that shown in FIG. 2.

In the embodiment depicted in FIG. 18, a rack 510 is housed within a cryogenic freezer 512. The rack includes, in this exemplary embodiment, three shelves 516 to 518. A single box 520 is shown to have been positioned on shelf 518, a single bag 522 is shown to have been located within that box 520. In this exemplary embodiment, a machine readable tag 524 is affixed to the freezer 512, a machine readable tag 526 is affixed to the rack 510, machine readable tags 528 to 532 are respectively affixed to shelves 514 to 518, a machine readable tag 534 is affixed to the box 520, whilst a machine readable tag 536 is affixed to the bag 522. Each of the machine readable tags may be separate or stand alone tags of the sort depicted in FIGS. 11 to 14. Maintenance of data in the database 238 of the relative locations and positions of shelves, boxes and bags within each rack stored in the freezer 510 enable the reading head to be used to firstly identify the freezer in which a desired sample is stored. Having thus identified the relevant freezer, the wand may be used to identify the relevant rack by reading the machine readable tag projecting therefrom through the opening in the freezer 512. Once the relevant rack has been identified, the rack can be temporarily removed from the freezer and each of the machine readable tags projecting from shelves can be read in order to identify the relevant shelf on which the desired box is stored. Once the relevant shelf is identified, machine readable tags projecting from each box can be read in order to locate the relevant box. Once the relevant box is identified, the machine readable tags projecting from bags located in that box can be then scanned in order to identify a desired bag. That bag can then be removed and the rack returned to the freezer.

Figure 19:
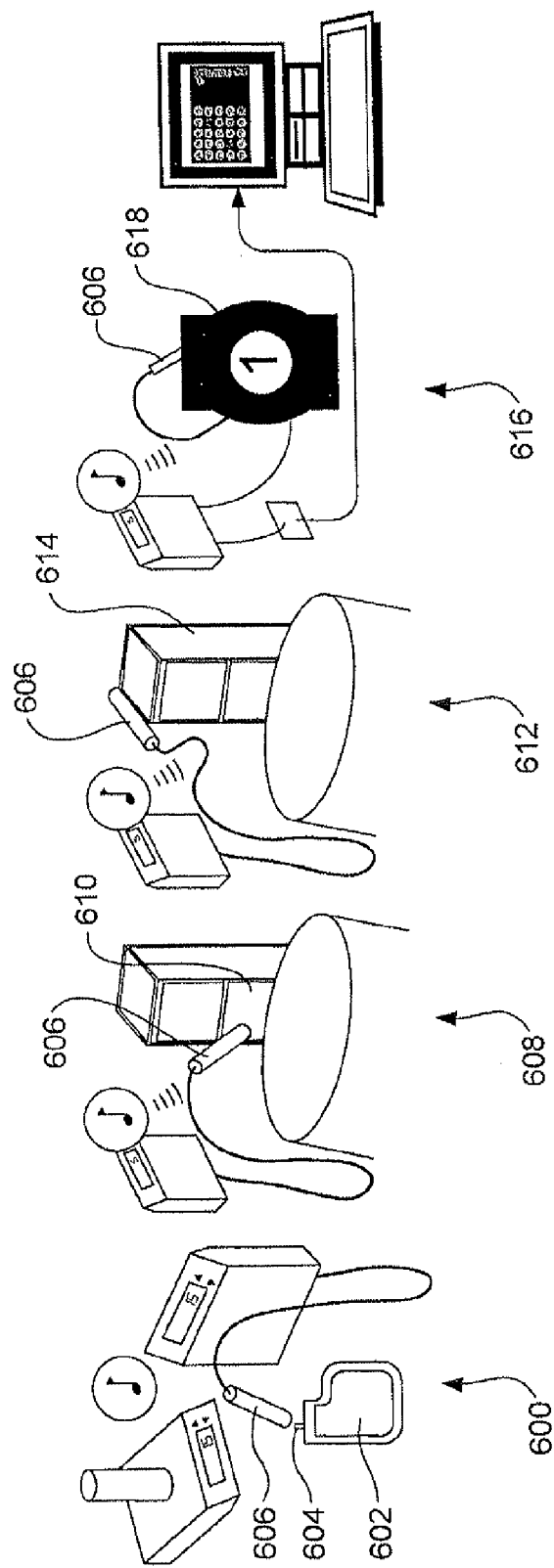
FIGS. 19 and 20 respectively show steps involved in logging in and retrieving sample storage bags from the temperature-controlled environment shown in FIG. 18.
Figure 20:
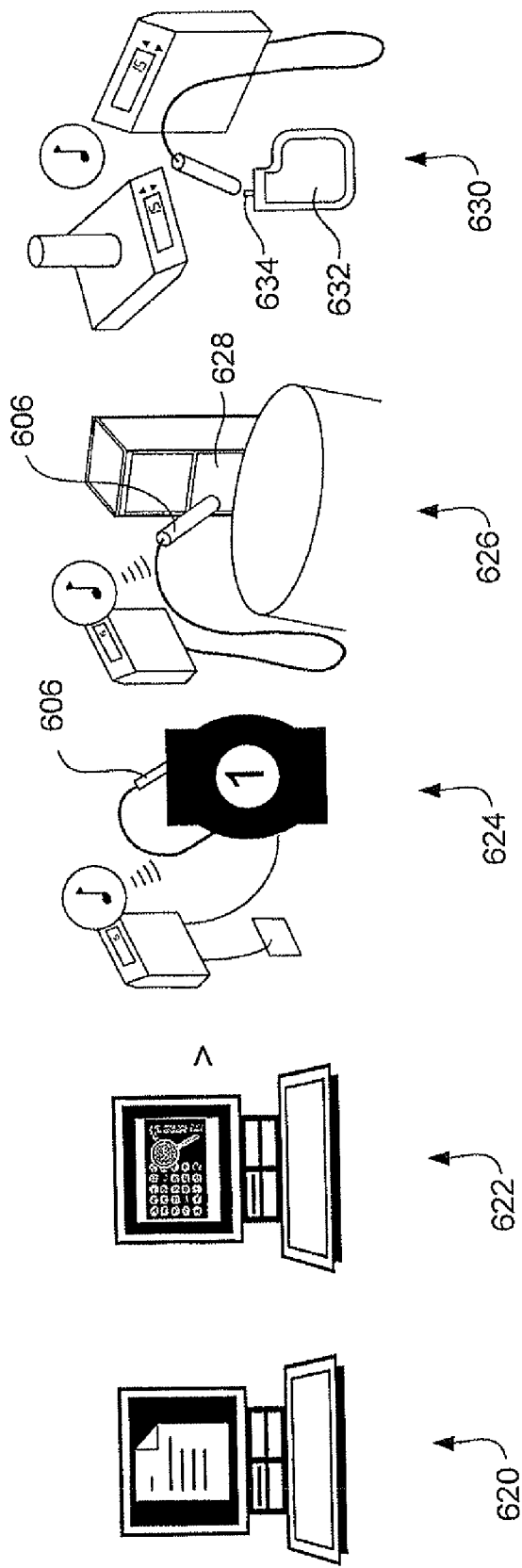

FIGS. 19 and 20 depict exemplary steps performed by the operator in the storage of samples in a freezer or like temperature controlled storage environment, and in the retrieval of a desired sample from that same environment. As depicted in FIG. 19, at step 600 a biological sample is stored within a bag 602, and the machine readable tag 604 projecting from that bag is then read using a reading head or wand 606. In step 608, the operator then uses the wand 606 to read a machine readable tag associated with a box 610 in which the bag 602 is desired to be stored. At step 612, the operator uses the reading head 606 to read a machine readable tag associated with the rack 614 in which the box is to be stored. Finally, at step 616 the operator uses the reading head 606 to read a machine readable tag associated with the freezer 618 in which the rack is placed. Data corresponding to the tag identifiers read during the read operations performed in steps 600, 608, 612 and 616 is then maintained in the database 238 (FIG. 2) and displayed to the operator via the display 240 (FIG. 2) in order to confirm to the operator where the sample maintained in the bag 602 is stored within the freezer 618.

When a sample is desired to be retrieved from the sample storage and monitoring system, details of the desired sample are entered by the user at step 620 (FIG. 20). Data is extracted from the database 238 at step 622 and displayed to the operator so that the operator is informed of the rack, box and bag ID in which the sample is stored. At step 624, the operator then uses the information obtained in step 622 to read the machine readable tags of the various freezers forming part of the sample monitoring and storage system to identify the correct freezer, and then the relevant rack within that identified freezer. At step 626, the operator removes the identified rack from the freezer and reads the machine readable tags associated with each of the boxes in that rack, in order to identify the box 628 indicated by the data retrieved by the operator at step 622. Finally, at step 630, the operator reads each of the machine readable tags projecting from the bags stored in the box 628 until the relevant bag 632 is identified from the identifier stored in the machine readable tag 634 projecting from that bag. That bag is then removed for further use or analysis by the operator, and the rack from which the bag was removed is then returned to the freezer.

Figure 21:
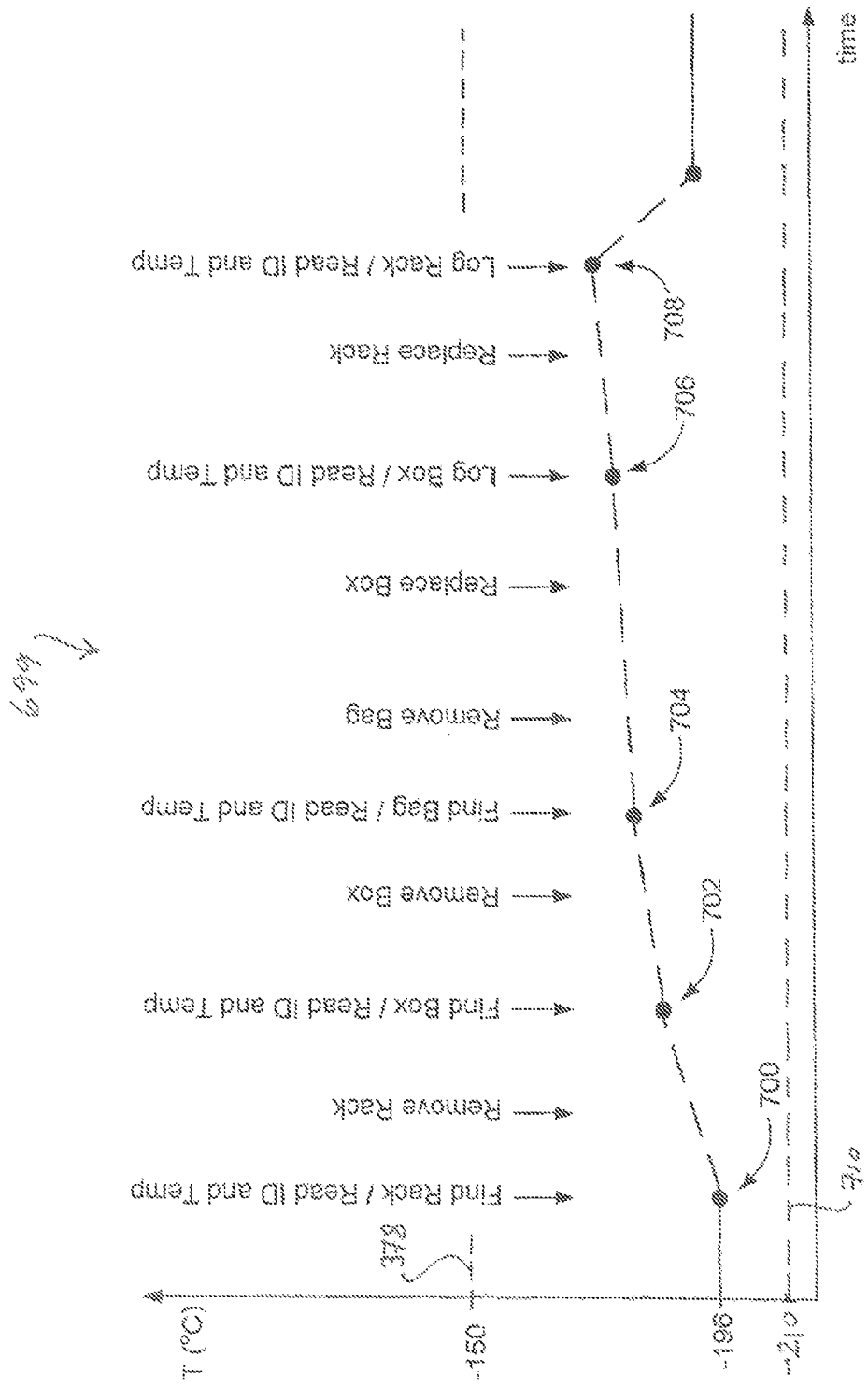
FIG. 21 is a graphical depiction of an exemplary thermal history of a biological sample stored and monitored by the system shown in FIG. 18.

FIG. 21 depicts an exemplary thermal history 699 of a sample maintained within a bag stored within a cryogenic storage tank, of the sort described in relation to FIGS. 19 and 20. In a "steady-state" condition, the temperature of samples in the tank is taken to be the ambient temperature within the tank. In this regard, a permanently mounted temperature sensor, such as the temperature sensor 270 depicted in FIG. 2, can be used to provide a continuous temperature reading.

When steps 620 and 622 shown in FIG. 20 have been performed, and an operator has determined that it would desirable to remove a particular bag from storage, the operator uses the reading head of the interrogator to locate the particular rack within an identified storage tank that currently houses the required bag. Once the particular rack is located at step 624 of FIG. 20, the interrogator acts to read not only the rack identifier encoded by the various resonant members forming part of the machine readable tag affixed to that rack, but also acts to read the temperature-dependent characteristic of at least one of those resonant members, namely the shift in resonant frequency as a function of temperature. This identifier and temperature reading operation results in a temperature measurement that should be identical to the temperature measurement provided from the temperature sensor reading the ambient temperature in the cryogenic storage tank, and is indicated in FIG. 21 as temperature data point 700.

Subsequent to the desired rack being located, the rack is then removed from the cryogenic storage tank. The operator then performs the operations described at step 626 in FIG. 20, namely using the reading head 606 of the interrogator to identify the box in which the desired sample is stored. When the desired box is located, the box identifier is read, together with the shift in resonant frequency of the resonant member/s of the machine readable tag. The temperature determined from this reading is indicated in FIG. 21 as temperature data point 702.

The box containing the desired sample is then removed from the rack, and the relevant bag storing the sample is identified by performing the operations described in relation to step 630 in FIG. 20. When the relevant bag is identified, the identifier of the bag is read, as well as the temperature dependent characteristic of the resonant member/s of the machine readable tag, resulting in a temperature data point 704 shown in FIG. 21.

The thus identified bag is then removed from the box, and the box replaced in the rack. The operator then performs a box login operation, in which the user reads the machine readable tag associated with the replaced box in order to read the box identifier and determine the temperature from the shift in resonant frequency of that machine readable tag. The temperature of the box that has just been inserted into the rack is logged, and is indicated in FIG. 21 as temperature data point 706.

The rack is then returned to the cryogenic storage tank and the operator then scans the machine readable tag associated with that returned rack in order to read the rack ID as well as the temperature dependent characteristic of the machine readable tag, in order to derive the temperature of the rack that has just been reinserted into the cryogenic storage tank. The corresponding temperature data point 708 is then added to the thermal history depicted in FIG. 21. Following reinsertion of the rack into the cryogenic storage tank, temperature data points to continue the thermal history are then taken from the temperature sensor indicating the ambient temperature within the cryogenic storage tank.

The graphical representation of the thermal history shown FIG. 21 also includes the upper temperature limit 378 (first shown in FIG. 10), as well as a lower temperature limit 710. In the event that any of the sample temperatures being monitored exceeds one of these limits, an alarm condition may be triggered by the central controller 236. The alarm condition may be displayed or otherwise brought to the attention of an operator in order that appropriate corrective action be taken. Alternatively, the central controller 236 may be configured to automatically take corrective action, for example by changing a temperature set-point signal used to regulate the storage temperature of the freezer 512 or tanks 200-206.

In other embodiments of the invention, the triggering of the alarm condition may simply result in the recordal in the database 238 of the sample temperature(s) having exceeds one of these limits without any alert being generated or corrective action occurring.

In yet other embodiments of the invention, two or more upper temperature limits and/or two or more lower temperature limits may be maintained in the database 238. The different temperature limits may correspond to different degrees of severity or danger. The central controller may be configured to provide different responses depending upon the particular temperature limit which is exceeded. For example, exceeding of a first upper or lower temperature limit may result in a display screen alert being displayed to an operator, whereas exceeding of a second upper or lower temperature limit may result in an audible alarm being generated.

From the foregoing, it will be appreciated that all samples stored in racks other than the rack that was removed from the cryogenic storage tank will be unaffected by that operation. However, the thermal history of samples stored in the rack which was removed will have been affected by that removal. FIG. 21 depicts a thermal history of samples stored in the rack which was removed and then re-inserted in the storage tank.

Typically, a bag that is removed from a rack is place in liquid nitrogen or another cooling medium. It will be appreciated that a temperature profile of a sample in that removed bag can be constructed from temperature data point 700 to 704, and continued by readings taken directly from the machine readable tag on the removed bag.

Whilst the invention has been described to this point in relation to the storage of biological samples in racks maintained within a cryogenic tank or freezer, it will be appreciated that a variety of other structures defining temperature controlled storage environments, sample storage containers and storage objects (such as shelves, boxes, racks and the like) for storing those containers or other storage objects may easily be envisaged.

Figure 22:
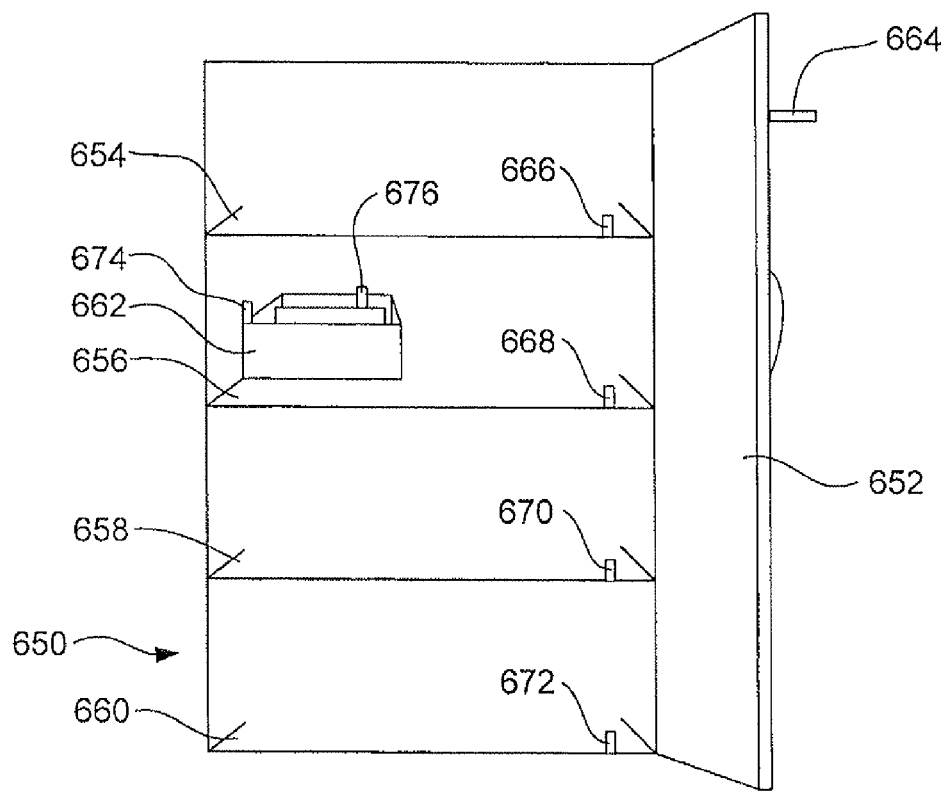
FIG. 22 is a schematic diagram depicting some elements of a further alternative temperature-controlled environment to that shown in FIG. 2.

For example, FIG. 22 depicts an exemplary freezer 650 including a front opening door 652, shelves 654 to 660 and an exemplary box 662 supported by one of those shelves. It will be appreciated that upon opening of the door, all shelves may be accessed and any machine readable tag projecting from a desired shelf, box stored on a shelf, or bag stored within a box may be accessed by an operator without removal of the desired box or bag from the freezer 650. In this exemplary embodiment, the freezer itself is provided with a machine readable tag 664, whilst the shelves are provided with machine readable tags 666 to 672, the box provided with machine readable tags 674 and the bag provided with machine readable tag 676.

This arrangement, the freezer/shelf/box/bag provides a hierarchical storage arrangement with four levels of nesting. It is to be understood that other hierarchical arrangements are possible with a greater or lesser extent of nesting.

Moreover, access to any of the machine readable tags associated with the containers or support objects or structures defining temperature controlled storage environments may be designed so that none or only some of the items stored within each structure need be removed in order to read relevant machine readable tag. For example, in the embodiment shown in FIG. 2, it is necessary to remove a storage rack from the cryogenic tank 200 in order to then remove an identified cassette from a rack, and to subsequently remove an identified bag from that cassette. In the embodiment depicted in FIG. 19, it is similarly necessary to remove a rack 510 from the freezer 512 in order to not only remove a relevant box and then a relevant bag from the freezer, but it is also necessary to remove the rack in order for an operator to read the machine readable tags of boxes and bags stored within the rack 510. However, in the embodiment of the invention shown in FIG. 20, no items are required to be removed from the freezer 650 in order for any of the machine readable tag to be read.

The above described system uses a machine readable tag including a plurality of resonant members to not only encode identification data, but also takes advantage of the temperature-dependant properties of such resonant members, in order to separately monitor the temperature of all samples stored in an temperature-controlled environment. In so do, the system enables a thermal history to be constructed for all samples stored in that temperature-controlled environment, thus ensuring the quality of those samples.

In other embodiments of the invention, different temperature-dependant characteristics of a machine readable tag may be read in order to track the thermal history of stored samples. Even in the case of machine readable tags including resonant members, the shift in resonant frequency of those resonant members in response to temperature is not the only temperature-dependant characteristic that can be measured. If the passive micro-electro-mechanical (MEMS) tag 14 were to be replaced by a MEMS capacitive sensor, the pulling voltage between capacitive plates of the sensor will have a temperature-dependant characteristic which can be measured. Similarly, if the tag 14 were to be replaced by a MEMS device having piezoelectric resonant members, the piezo resistance properties of the members will have a temperature-dependant characteristic which can be measured. In yet other embodiments of the invention, the tag 14 may be replaced with an active or passive RFID tag which does not necessarily include a MEMS structure, such as a CMOS based RFID tag. For example, a resistor having a temperature-dependant value could form part of the tag and that value read in order to track the thermal history of stored samples. Alternatively, an antenna forming part of the tag may have a temperature dependant impedance which is detectable by a tune antenna. A skilled addressee will be able to conceive of a variety of other temperature-dependant characteristics of machine readable tags which are suitable for use in the context of the present invention.

Moreover, the above-described system for storing and monitoring samples minimises the need for operators to handle stored samples, and minimises the physical discomforts and inconveniences associated with such handling. For example, in a low temperature environment, freezer of a user's fingers or hands, and the need for a pause in order to change handling gloves is minimised. The system also enables the consistent handling of samples, eliminating the need to touch containers such as bags and only requiring their removal of tightly packed boxes or other structures when necessary. Physical and thermal impact on the stored samples is minimised during the storage and searching processes. An operator is able to maintain the quality of a stored sample when removed from a temperature controlled environment.

The above described system further enables a biological sample to be identified without requiring removal from its storage environment. Moreover, this system enable the tracking of the temperature experienced by the samples upon interrogation without the need to add another component to the rack in which the biological sample is stored. The presence of the biological samples is also able to be validated, and an audit able to be conducted, without requiring visual inspection of every biological sample, cassette or rack in the cryogenic tanks.

Future patent applications may be filed in Australia or overseas on the basis of or claiming priority from the present application. It is to be understood that the following provisional claims are provided by way of example only, and are not intended to limit the scope of what may be claimed in any such future application. Features may be added to or omitted from the provisional claims at a later date so as to further define or re-define the invention or inventions.

The invention claimed is:

1. A method of maintaining a thermal history of biological samples stored in a temperature-controlled sample storage system, the system including one or more containers each storing one of the samples; one or more storage objects each housing one or more containers or one or more second storage objects; one or more structures defining a temperature-controlled storage environment and housing the one or more storage objects; machine readable tags each of which is associated with a separate container and storage object, each tag encoding an identification code and having a temperature-dependant characteristic; and an interrogator for reading the identification code and the temperature-dependant characteristic, the method including the steps of:
    a) monitoring the temperature in each temperature-controlled storage environment;
    b) interrogating a database to determine one or more specific storage objects housing a particular container within a specific structure;
    c) locating one of the specific storage objects housing the particular container by reading the identification code of the machine-readable tag associated with that specific storage object;
    d) reading the value of the temperature dependant characteristic of the machine-readable tag associated with the specific storage object located in step c);
    e) storing the read identification code and value of the temperature-dependant characteristic in the database;
    f) removing the particular container, or another of the specific storage objects in which the particular container is stored, from the storage object located in step b);
    g) repeat steps c) to f) until the particular container is removed; and
    h) returning the one or more specific storage objects to the specific structure.

2. A method according to claim 1, and further including the step of:
    determining whether any of the values of the temperature dependant characteristic exceed a temperature limit.

3. A method according to claim 2, and further including the step of:
    triggering an alarm condition when the value exceeds the temperature limit.

4. A method according to claim 1, and further including the step of:
    determining whether any of the values of the temperature dependant characteristic exceeds any of a plurality of temperature limits.

5. A method according to claim 4, and further including the step of:
    triggering an alarm condition when the value exceeds any one of the temperature limits.

6. A method according to claim 5, and further including the step of:
    providing a different response depending upon which of the temperature limits are exceeded.

7. A method according to claim 1, and further including the step of:
    prior to step c), locating the specific structure housing the particular container by reading the identification code of the machine-readable tag associated with that structure.

8. A method according to claim 1, and further including the step of retrievably housing each container in the structure by:
    reading the identification code of the machine-readable tag associated with each container;

reading the identification code of the machine-readable tag associated with each storage object in which the container is housed;

storing the read identification codes in the database for subsequent interrogation.

9. A method according to claim 1, wherein each machine readable tag includes a plurality of resonant members.

10. A method according to claim 9, wherein at least one of the resonant members has the temperature-dependant characteristic.

11. A method according to claim 9, wherein the resonant members have different resonant frequencies from each other.

12. A method according to claim 9, wherein the resonant members are vibrated by a Lorentz-type force on application of an excitation signal to the tag.

13. A method according to claim 9, wherein the temperature-dependant characteristic is a shift in resonant frequency of the at least one resonant member as a function of temperature.

14. A method according to claim 9, wherein a first coil antenna is coupled to the plurality of resonant members, wherein the interrogator includes signal processing circuitry and a reading head in communication with signal processing circuitry, and wherein the reading head including an interrogation coil, the method further including the steps of:

positioning the interrogation coil proximate the coil antenna; and generating an interrogation signal in the interrogation coil so as to induce an excitation signal in the coil antenna.

15. A method according to claim 14, wherein the step of positioning the interrogation coil proximate the coil antenna includes locating one of the interrogation coil and the antenna coil inside the other during tag reading.

16. A method according to claim 15, wherein one or both of the interrogation coil and the antenna coil have a helical form.

17. A method according to claim 14, wherein the step of positioning the interrogation coil proximate the coil antenna includes concentrically locating the interrogation coil and the antenna coil during tag reading.

* * * * *